US008021833B2

(12) United States Patent
Yu et al.

(10) Patent No.: US 8,021,833 B2
(45) Date of Patent: Sep. 20, 2011

(54) METHOD FOR REDUCING HIV VIRAL BUDDING BY ADMINISTERING A VPS28-SPECFIC ANTIBODY THAT DISRUPTS GAG-TSG101-VPS28 BINDING INTERACTIONS

(75) Inventors: Xiao-Fang Yu, Baltimore, MD (US); Bindong Liu, Nashville, TN (US); Limin Li, Potomac, MD (US)

(73) Assignees: Functional Genetics, Inc., Gaithersburg, MD (US); Johns Hopkins University, Baltimore, MD (US)

( * ) Notice: Subject to any disclaimer, the term of this patent is extended or adjusted under 35 U.S.C. 154(b) by 884 days.

(21) Appl. No.: 10/545,426

(22) PCT Filed: Feb. 12, 2004

(86) PCT No.: PCT/US2004/004518

§ 371 (c)(1), (2), (4) Date: Aug. 28, 2006

(87) PCT Pub. No.: WO2004/071462

PCT Pub. Date: Aug. 26, 2004

(65) Prior Publication Data

US 2007/0082335 A1 Apr. 12, 2007

Related U.S. Application Data

(60) Provisional application No. 60/446,909, filed on Feb. 12, 2003.

(51) Int. Cl.

| | |
|---|---|
| *C12Q 1/70* | (2006.01) |
| *A61K 39/00* | (2006.01) |
| *A61K 39/395* | (2006.01) |
| *A61K 39/42* | (2006.01) |
| *A61K 39/21* | (2006.01) |

(52) U.S. Cl. ... 435/5; 424/139.1; 424/156.1; 424/160.1; 424/208.1

(58) Field of Classification Search ........................ None
See application file for complete search history.

(56) References Cited

U.S. PATENT DOCUMENTS

| | | | |
|---|---|---|---|
| 4,190,496 | A | 2/1980 | Rubenstein et al. |
| 4,376,110 | A | 3/1983 | David et al. |
| 4,745,051 | A | 5/1988 | Smith et al. |
| 4,946,778 | A | 8/1990 | Ladner et al. |
| 4,980,286 | A | 12/1990 | Morgan et al. |
| 5,272,071 | A | 12/1993 | Chappel |
| 5,968,502 | A | 10/1999 | Treco et al. |
| 5,981,214 | A | 11/1999 | Skoultchi |
| 2002/0173622 | A1 | 11/2002 | Wettstein et al. |
| 2002/0177207 | A1 | 11/2002 | Sugiyama et al. |

FOREIGN PATENT DOCUMENTS

| | | |
|---|---|---|
| WO | WO 88/04300 | 6/1988 |
| WO | WO 91/06667 | 5/1991 |
| WO | WO 92/06180 | 4/1992 |
| WO | WO 92/20316 | 11/1992 |
| WO | WO 92/22635 | 12/1992 |
| WO | WO 93/14188 | 7/1993 |
| WO | WO 93/20221 | 10/1993 |
| WO | WO 94/08598 | 4/1994 |
| WO | WO 94/12650 | 6/1994 |
| WO | WO 99/15650 | 4/1999 |
| WO | WO 02/072790 | 9/2002 |

OTHER PUBLICATIONS

Letvin, N. L., and B. D. Walker, 2003, Immunopathogenesis and immunotherapy in AIDS virus infections, Nat. Med. 9(7):861-866.*
Montefiori, D. C., 2005, Neutralizing antibodies take a swipe at HIV in vivo, Nat. Med. 11(6):593-594.*
Trkola, A., et al., 2005, Delay of HIV-1 rebound after cessation of antiretroviral therapy through passive transfer of human neutralizing antibodies, Nat. Med. 11(6):615-622.*
Wilson, J. A., et al., 2001, Ebola virus: the search for vaccines and treatments, Cell. Mol. Life Sci. 58:1826-1841.*
Geisbert, T. W., et al., 2002, Evaluation in nonhuman primates of vaccines against ebola virus, Emerg. Infect. Dis. 8(5):503-507.*
Oswald, W. B., et al., 2007, Neutralizing antibody fails to impact the course of ebola virus infection in monkeys, PLoS Pathogens, 3(1):62-66.*
Jahrling, P. B., et al., 2007, Ebola hemorrhagic fever: evaluation of passive immunotherapy in nonhuman primates, J. Infect. Dis. 196(Suppl. 2):S400-3.*
Chua, H.-H., et al., 2007, Role of the TSG101 gene in Epstein-Barr virus late gene transcription, J. Virol. 81(5):2459-2471.*
Eastman, S. W., et al., 2005, Identification of human VPS37C, a component of endosomal sorting complex required for transport-I important for viral budding, J. Biol. Chem. 280(1):628-636.*
Pincetic, A., et al., 2008, Avian sarcoma viruses and human immunodeficiency virus, type 1 use different subsets of ESCRT proteins to facilitate the budding process, J. Biol. Chem. 483(44):29822-29830.*
Irie, T., et al., 2004, Budding of PPxY-containing rhabdoviruses is not dependent on host proteins TGS101 and VPS4A, J. Virol. 78(6):2657-2665.*
Bonnin, E., et al., 2004, Generation of functional scFv intrabodies for triggering anti-tumor immunity, Methods 34(2):225-232.*
Bishop, N., and P. Woodman, 2001, TSG101/mammalian VPS23 and mammalian VPS28 interact directly and are recruited to VPS4-induced endosomes, J. Biol. Chem. 276(15):11735-11742.*

(Continued)

*Primary Examiner* — Jeffrey Parkin
(74) *Attorney, Agent, or Firm* — Steven B. Kelber

(57) ABSTRACT

The importance of interaction between TSG101 and Vps28 in the release of HIV-1 and other viruses is disclosed. Suppressing or interfering in this interaction may inhibit HIV-1 virion release from infected cells. Agents that modulate this interaction include antibodies that bind to Vps28, polypeptides that bind to Vps28, and nucleic acids that may be used in gene therapy to interfere with the expression of wild type Vps28. Administration of such agents in vitro for screening and diagnostic purposes, and in vivo for diagnostic and therapeutic purposes, is disclosed.

3 Claims, 8 Drawing Sheets

OTHER PUBLICATIONS

Figure 1A:
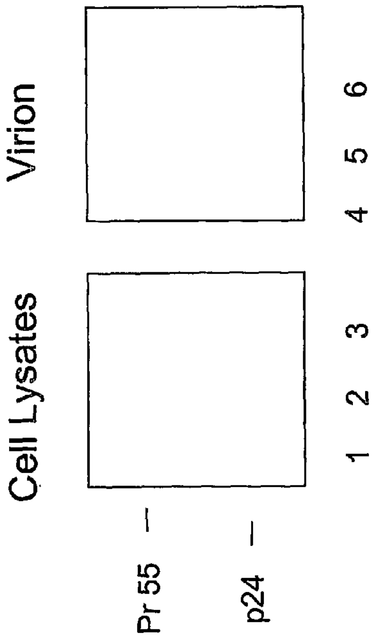

Bishop, N., and P. Woodman. 2001. TSG101/Mammalian VPS23 and Mammalian VPS28 Interact Directly and are Recruited to VPS4-induced endosomes. J. Biol. Chem. 276(15):11735-11742.*
Martin-Serrano et al., "Role of ESCRT-I in Retroviral Budding", *Journal of Virology*, 77(8):4794-4804 (2003).
Tanzi et al., "Equine Infectious Anemia Virum Utilizes Host Vesicular Protein Sorting Machinery during Particle Release", *Journal of Virology*, 77(15):8440-8447 (2003).
Haseloff, et al., "Simple RNA Enzymes with New and Highly Specific Endoribonuclease Activities," Nature, vol. 334, pp. 585-591 (1988).
Hay, et al., "Bacteriophage Cloning and *Escherichia coli* Expression of a Human IgM Fab," Hum. Antibod. Hybridomas, vol. 3, pp. 81-85 (1992).
Houghten, et al., "Generation and Use of Synthetic Peptide Combinatorial Libraries for Basic Research and Drug Discovery," Nature, vol. 354, pp. 84-86 (1991).
Huang, et al., "p6$^{Gag}$ is Required for Particle Production from Full-Length Human Immunodeficiency Virus Type I Molecular Clones Expressing Protease," Journal of Virology, vol. 69, No. 11, pp. 6810-6818 (1995).
Huse, et al., "Generation of a Large Combinatorial Library of the Immunoglobulin Repertoire in Phage Lambda," Science, vol. 246, pp. 1275-1281 (1989).
Huston, et al., "Protein Engineering of Antibody Binding Sites: Recovery of Specific Activity in an Anti-Digoxin Single-Chain Fv Analogue Produced in *Escherichia coli*," Proc. Natl. Acad. Sci. USA, vol. 85, pp. 5879-5883 (1988).
Inouye, et al., "Up-Promoter Mutations in the Ipp Gene of *Escherichia coli*," Nucleic Acids Research, vol. 13, No. 9, pp. 3101-3110 (1985).
Izant, et al., "Inhibition of Thymidine Kinase Gene Expression by Anti-Sense RNA: A Molecular Approach to Genetic Analysis," Cell, vol. 36, pp. 1007-1015 (1984).
Janknecht, et al., "Rapid and Efficient Purification of Native Histidine-Tagged Protein Expressed by Recombinant Vaccinia Virus," Proc. Natl. Acad. Sci. USA, vol. 88, pp. 8972-8976 (1991).
Kang, et al., "Zinc Finger Proteins as Designer Transcription Factors," The Journal of Biological Chemistry, vol. 275, No. 12, pp. 8742-8748 (2000).
Katzmann, et al., "Ubiquitin-Dependent Sorting into the Multivesicular Body Pathway Requires the Function of a Conserved Endosomal Protein Sorting Complex. ESCRT-1," Cell, vol. 106, pp. 145-155 (2001).
Kiem, et al., "Retrovirus-Mediated Gene Transduction Into Canine Peripheral Blood Repopulating Cells," Blood, vol. 83, No. 6, pp. 1467-1473 (1994).
Kikyo, et al., "Active Remodeling of Somatic Nuclei in Egg Cytoplasm by the Nucleosomal ATPase ISWI," Science, vol. 289, pp. 2360-2362 (2000).
Kim, et al., "Transcriptional Repression by Zinc Finger Peptides," The Journal of Biological Chemistry, vol. 272, No. 47, pp. 29795-29800 (1997).
Kim, et al., "Getting a Handhold on DNA: Design of Poly-Zinc Finger Proteins with Femtomolar Dissociation Constants," Proc. Natl. Acad. Sci. USA, vol. 95, pp. 2812-2817 (1998).
Kim, et al., "Design of TATA Box-Binding Protein/Zinc Finger Fusions for Targeted Regulation of Gene Expression," Proc. Natl. Acad. Sci. USA, vol. 94, pp. 3616-3620 (1997).
Kodo, et al.. "Antibody Synthesis by Bone Marrow Cells in Vitro Following Primary and Booster Tetanus Toxoid Immunization in Humans," J. Clin. Invest., vol. 73, pp. 1377-1384 (1984).
Kohler, et al., "Continuous Cultures of Fused Cells Secreting Antibody of Predefined Specificity," Nature, vol. 256, pp. 495-497 (1975).
Koller, et al., "Inactivating the $\beta_2$-Microglobulin Locus in Mouse Embryonic Stem Cells by Homologous Recombination." Proc. Natl. Acad. Sci. USA, vol. 86, pp. 8932-8935 (1989).
Kozbor, et al., "The Production of Monoclonal Antibodies from Human Lymphocytes," Immunology Today, vol. 4, No. 13, pp. 72-79 (1983).
Kozarsky, et al., "Gene Therapy: Adenovirus Vectors," Current Opinion in Genetics and Development, vol. 3, pp. 499-503 (1993).
Krempler, et al., "Targeted Deletion of the Tsg101 Gene Results in Cell Cycle Arrest at $G_1$/S and p53-Independent Cell Death," The Journal of Biological Chemistry, vol. 277, No. 45, pp. 43216-43223 (2002).
Lam, et al., "A New Type of Synthetic Peptide Library for Identifying Ligand-Binding Activity," Nature, vol. 354, pp. 82-84 (1991).
Li, et al., "tsg101: A Novel Tumor Susceptibility Gene Isolated by Controlled Homozygous Functional Knockout of Allelic Loci in Mammalian Cells," Cell, vol. 85, pp. 319-329 (1996).
Li, et al., "A TSG101/MDM2 Regulatory Loop Modulates MDM2 Degradation and MDM2/p53 Feedback Control," Proc. Natl. Acad. Sci., vol. 98, No. 4, pp. 1619-1624 (2001).
Liu, et al., "Design of Polydactyl Zinc-Finger Proteins for Unique Addressing within Complex Genomes," Proc. Natl. Acad. Sci. USA. vol. 94, pp. 5525-5530 (1997).
Liu, et al., "Regulation of an Endogenous Locus Using a Panel of Designed Zinc Finger Proteins Targeted to Accessible Chromatin Regions," The Journal of Biological Chemistry, vol. 276. No. 14, pp. 11323-11334 (2001).
Llewellyn, et al., "Structure and Expression of an Alcohol Dehydrogenase 1 Gene from Pisum Sativum (cv. "Greenfeast")," J. Mol. Biol., vol. 195, pp. 115-123 (1987).
Loeffler, et al., "Gene Transfer into Primary and Established Mammalian Cell Lines with Lipopolyamine-Coated DNA," Methods in Enzymology, vol. 217, pp. 599-619 (1993).
Logan, et al., "Adenovirus Tripartite Leader Sequence Enhances Translation of mRNAs Late After Infection," Proc. Natl. Acad. Sci. USA, vol. 81, pp. 3655-3659 (1984).
Lowy, et al., "Isolation of Transforming DNA: Cloning the Hamster aprt Gene," Cell, vol. 22, pp. 817-823 (1980).
Martin-Serrano et al., "HIV-1 and Ebola Virus Encode Small Peptide Motifs that Recruit Tsg101 to Sites of Particle Assembly to Facilitate Egress," Nature Medicine, vol. 7, No. 12, pp. 1313-1319 (2001).
Mastrangeli, et al., "Diversity of Airway Epithelial Cell Targets for in Vivo Recombinant Adenovirus-Mediated Gene Transfer," The Journal of Clinical Investigation, vol. 91, pp. 225-234 (1993).
Colbere-Garapin, et al, "A New Dominant Hybrid Selective Marker for Higher Eukaryotic Cells," J. Mol. Biol., vol. 150, pp. 1-14 (1981).
Cote, et al., "Generation of Human Monoclonal Antibodies Reactive with Cellular Antigens," Proc. Natl. Acad. Sci. USA, vol. 80, pp. 2026-2030 (1983).
Cole, et al., "The EBV-Hybridoma Technique and its Application to Human Lung Cancer," Monoclonal Antibodies and Cancer Therapy, vol. 76, No. 1, pp. 77-96 (1985).
Demirov, et al., "The Late Domain of Human Immunodeficiency Virus Type 1 p6 Promotes Virus Release in a Cell Type-Dependent Manner," Journal of Virology, pp. 105-117 (2002).
Demirov, et al., "Overexpression of the N-Terminal Domain of TSG101 Inhibits HIV-1 Budding by Blocking Late Domain Function," Proc. Natl. Acad. Sci., vol. 99, No. 2. pp. 955-960 (2002).
Dettenhofer et al., "Proline Residues in Human Immunodeficiency Virus Type 1 p6$^{Gag}$ Exert a Cell Type-Dependent Effect on Viral Replication and Virion Incorporation of Pol Proteins," Journal of Virology, vol. 73, No. 6, pp. 4696-4704 (1999).
Dexter, et al., "Conditions Controlling the Proliferation of Haemopoietic Stem Cells in Vitro," J. Cell. Physiol., vol. 91, pp. 335-344 (1976).
Elbashir, et al., "Duplexes of 21-Nucleotide RNAs Mediate RNA Interference in Cultured Mammalian Cells," Nature, vol. 411, pp. 494-498 (2001).
Fire, et al., "Potent and Specific Genetic Interference by Double-Stranded RNA in *Caenorhabditis elegans*," Nature, vol. 391, pp. 806-811 (1998).
Fuchs, et al., "Targeting Recombinant Antibodies to the Surface of *Escherichia coli*: Fusion to a Peptidoglycan Associated Lipoprotein," Biotechnology, vol. 9, pp. 368-372 (1991).
Garrus, et al., "Tsg101 and the Vacuolar Protein Sorting Pathway are Essential for HIV-1 Budding," Cell, vol. 107, pp. 55-65 (2001).
Goldspiel, et al., "Human Gene Therapy," Clinical Pharmacy, vol. 12, pp. 488-505 (1993).

Gottlinger, et al., "Effect of Mutations Affecting the p6 gag Protein on Human Immunodeficiency Virus Particle Release." Proc. Natl. Acad. Sci. USA, vol. 88, pp. 3195-3199 (1991).
Grant, "Dissecting the Mechanisms of Posttranscriptional Gene Silencing: Divide and Conquer," Cell, vol. 96, pp. 303-306 (1999).
Gregory, "Transcription and Chromatin Converge: Lessons from Yeast Genetics," Current Opinion in Genetics & Development, vol. 11, pp. 142-147 (2001).
Greisman, et al.. "A General Strategy for Selecting High-Affinity Zinc Finger Proteins for Diverse DNA Target Sites," Science, vol. 275, pp. 657-661 (1997).
Griffiths, et al., "Human Anti-Self Antibodies with High Specificity from Phage Display Libraries," The EMBO Journal, vol. 12, No. 2, pp. 725-734 (1993).
Grossman, et al., "Retroviruses: Delivery Vehicle to the Liver," Current Opinion in Genetics & Development, vol. 3, pp. 110-114 (1993).
Guo, et al., "par-1, a Gene Required for Establishing Polarity in *C. elegans* Embryos, Encodes a Putative Ser/Thr Kinase that is Asymmetrically Distributed," Cell, vol. 81, pp. 611-620 (1995).
Hanahan. "Studies on Transformation of *Escherichia coli* with Plasmids," J. Mol. Biol., vol. 166, pp. 557-580 (1983).
Babst, et al., "Mammalian Tumor Susceptibility Gene 101 (TSG101) and the Yeast Homologue, Vps23p, Both Function in Late Endosomal Trafficking," Traffic, vol. 1, pp. 248-258 (2000).
Bass, "Double-Stranded RNA as a Template for Gene Silencing," Cell, vol. 101, pp. 235-238 (2000).
Been, et al., "One Binding Site Determines Sequence Specificity of Tetrahymena Pre-rRNA Self-Splicing, Trans-Splicing, and RNA Enzyme Activity," Cell, vol. 47, pp. 207-216 (1986).
Beerli, et al., "Toward Controlling Gene Expression at Will: Specific Regulation of the erbB-2/HER-2 Promoter by Using Polydactyl Zinc Finger Proteins Constructed from Modular Building Blocks," Proc. Natl. Acad. Sci. USA. vol. 95, pp. 14628-14633 (1998).
Beerli, et al., "Positive and Negative Regulation of Endogenous Genes by Designed Transcription Factors," Proc. Natl. Acad. Sci., vol. 97, No. 4, pp. 1495-1500 (2000).
Berg, et al., "The Galvanization of Biology: A Growing Appreciation for the Roles of Zinc," Science, vol. 271, pp. 1081-1085 (1996).
Berg, "Letting Your Fingers do the Walking," Nature Biotechnology, vol. 15, p. 323 (1997).
Bird, et al., "Single-Chain Antigen-Binding Proteins," Science, vol. 242, pp. 423-426 (1988).
Bishop, et al., "Mammalian Class E vps Proteins Recognize Ubiquitin and Act in the Removal of Endosomal Protein-Ubiquitin Conjugates," The Journal of Cell Biology, vol. 157, pp. 91-101 (2002).
Bishop, et al., "TSG101/Mammalian VPS23 and Mammalian VPS28 Interact Directly and are Recruited to VPS4-Induced Endosomes." The Journal of Biological Chemistry, vol. 276, No. 15, pp. 11735-11742 (2001).
Bitter, et al., "Expression and Secretion Vectors for Yeast," Methods in Enzymology, vol. 153, pp. 516-545 (1987).
Boesen, et al., "Circumvention of Chemotherapy-Induced Myelosuppression by Transfer of the mdr 1 Gene," Biotherapy, vol. 6, pp. 291-302 (1994).
Bout, et al., "Lung Gene Therapy: In Vivo Adenovirus-Mediated Gene Transfer to Rhesus Monkey Airway Epithelium," Human Gene Therapy, vol. 5, pp. 3-10 (1994).
Butler, "The Amplified ELISA: Principles of and Applications for the Comparative Quantitation of Class and Subclass Antibodies and the Distribution of Antibodies and Antigens in Biochemical Separates," Methods in Enzymology, vol. 73, pp. 482-523 (1981).
Choo, et al., "Promoter-Specific Activation of Gene Expression Directed by Bacteriophage-Selected Zinc Fingers," J. Mol. Biol., vol. 273, pp. 525-532 (1997).
Cline, "Perspectives for Gene Therapy: Inserting New Genetic Information into Mammalian Cells by Physical Techniques and Viral Vectors." Pharmac. Ther., vol. 29, pp. 69-92 (1985).
Clowes, et al., "Long-Term Biological Response of Injured Rat Carotid Artery Seeded with Smooth Muscle Cells Expressing Retrovirally Introduced Human Genes," J. Clin. Invest., vol. 93, pp. 644-651 (1994).
Robinson. "Gene Therapy—Proceeding from Laboratory to Clinic," Tibtech, vol. 11, pp. 155-215 (1993).
Miller, et al., "Use of Retroviral Vectors for Gene Transfer and Expression," Methods in Enzymology, vol. 217, pp. 581-599 (1993).
Morgan, et al., "Human Gene Therapy," Annu. Rev. Biochem, vol. 62, pp. 191-217 (1993).
Morrison, et al., "Chimeric Human Antibody Molecules: Mouse Antigen-Binding Domains with Human Constant Region Domains," Proc. Natl. Acad. Sci. USA, vol. 81, pp. 6851-6855 (1984).
Moyret-Lalle, et al., "p53 Induction Prevents Accumulation of Aberrant Transcripts in Cancer Cells," Cancer Research, vol. 61, pp. 486-488 (2001).
Mulligan, et al., "Selection for Animal Cells that Express the *Escherichia coli* Gene Coding for Xanthine-Guanine Phosphoribosyltransferase," Proc. Nat. Acad. Sci. USA, vol. 78, No. 4, pp. 2072-2076 (1981).
Mulligan, "The Basic Science of Gene Therapy," Science, vol. 260, pp. 926-932 (1993).
Neuberger, et al., "Recombinant Antibodies Possessing Novel Effector Functions," Nature, vol. 312, pp. 604-608 (1984).
Oh, et al., "Negative Regulation of Cell Growth and Differentiation by TSG101 through Association with p21 $^{Cip1/WAF1}$," Proc. Natl. Acad. Sci., vol. 99, No. 8, pp. 5430-5435 (2002).
O'Hare, et al., "Transformation of Mouse Fibroblasts to Methotrexate Resistance by a Recombinant Plasmid Expressing a Prokaryotic Dihydrofolate Reductase," Proc. Natl. Acad. Sci. USA, vol. 78, No. 3, pp. 1527-1531 (1981).
Paddison,et al., "Short Hairpin RNAs (shRNAs) Induce Sequence-Specific silencing in Mammalian Cells," Genes & Development, vol. 16, pp. 948-958 (2002).
Paddison, et al., "Stable Suppression of Gene Expression by RNAi in Mammalian Cells," Proc. Natl. Acad. Sci., vol. 99, No. 3, pp. 1443-1448 (2002).
Parent, et al., "Positionally Independent and Exchangeable Late Budding Functions of the Rous Sarcoma Virus and Human Immunodeficiency Virus Gag Proteins," Journal of Virology, vol. 69, No. 9, pp. 5455-5460 (1995).
Patnaik, et al., "Ubiquitin is Part of the Retrovirus Budding Machinery," Proc. Natl. Acad. Sci., vol. 97, No. 24, pp. 13069-13074 (2000).
Pavletich, et al., "Zinc Finger-DNA Recognition: Crystal Structure of a Zif268-DNA Complex at 2.1 A," Science, vol. 252. No. 5007, pp. 809-817 (1991).
Petcherski, et al., "LAG-3 is a Putative Transcriptional Activator in the C. Elegans Notch Pathway," Nature, vol. 405, pp. 364-368 (2000).
Pittelkow, et al., "New Techniques for the in Vitro Culture of Human Skin Keratinocytes and Perspectives on Their Use for Grafting of Patients with Extensive Burns," Mayo Clin. Proc., vol. 61, pp. 771-777 (1986).
Platt, et al., "Independent Regulation of Adipose Tissue-Specificity and Obesity Response of the Adipsin Promoter in Transgenic Mice," The Journal of Biological Chemistry, vol. 269, No. 46, pp. 28558-28562 (1994).
Pomillos, et al., "Structure and Functional Interactions of the Tsg101 UEV Domain," The EMBO Journal, vol. 21. No. 10, pp. 2397-2406 (2002).
Pornillos, et al., "Structure of the Tsg101 UEV Domain in Complex with the PTAP Motif of the HIV-1 p6 Protein," Nature Structural Biology, vol. 9, No. 11, pp. 812-817 (2002).
Puffer, et al., "Equine Infectious Anemia Virus Utilizes a YXXL Motif within the Late Assembly Domain of the Gag P9 Protein," Journal of Virology, vol. 71, No. 9, pp. 6541-6546 (1997).
Rebar, et al., "Zinc Finger Phage: Affinity Selection of Fingers with New DNA-Binding Specificities," Science, vol. 263, pp. 671-673 (1994).
Rheinwald. "Serial Cultivation of Normal Human Epidermal Keratinocytes." Methods in Cell Biology, vol. 2IA, pp. 229-255 (1980).
Rhodes, et al., "Zinc Fingers," Scientific American, pp. 56-65 (1993).
Robertson, et al., "DNA Methylation in Health and Disease," Nature Reviews, vol. 1, pp. 11-19 (2000).
Rosenberg, et al., "Production of Phenocopies by Kruppel Antisense RNA Injection into Drosophila Embryos," Nature, vol. 313, pp. 703-706 (1985).

Rosenfeld, et al., "Adenovirus-Mediated Transfer of a Recombinant αl-Antitrypsin Gene to the Lung Epithelium in Vivo," Science, vol. 252, pp. 431-434 (1991).
Rosenfeld, et al., "In Vivo Transfer of the Human Cystic Fibrosis Transmembrane Conductance Regulator Gene to the Airway Epithelium," Cell, vol. 68, pp. 143-155 (1992).
Ruland, et al., "p53 Accumulation, Defective Cell Proliferation, and Early Embryonic Lethality in Mice Lacking tsg101," Proc. Natl. Acad. Sci., vol. 98, No. 4, pp. 1859-1864 (2001).
Ruther, et al., "Easy Identification of cDNA Clones," The EMBO Journal, vol. 2, No. 10, pp. 1791-1794 (1983).
Salmons, et al., "Targeting of Retroviral Vectors for Gene Therapy," Human Gene Therapy, vol. 4, pp. 129-141 (1993).
Santerre, et al., "Expression of Prokaryotic Genes for Hygromycin B and G418 Resistance as Dominant-Selection Markers in Mouse L Cells," Gene, vol. 30, pp. 147-156 (1984).
Schubert, et al., "Proteasome Inhibition Interferes with Gag Polyprotein Processing, Release, and Maturation of HIV-1 and HIV-2," Proc. Natl. Acad. Sci., vol. 97, No. 24, pp. 13057-13062 (2000).
Smith, et al., "Molecular Engineering of the Autographa California Nuclear Polyhedrosis Virus Genome: Deletion Mutations Within the Polyhedrin Gene," Journal of Virology, vol. 46, No. 2, pp. 584-593 (1983).
Songyang, et al., "SH2 Domains Recognize Specific Phosphopeptide Sequences," Cell, vol. 72, pp. 767-778 (1993).
Stemple, et al., "Isolation of a Stem Cell for Neurons and Glia from the Mammalian Neural Crest," Cell, vol. 71, pp. 973-985 (1992).
Strack, et al., "A Role for Ubiquitin Ligase Recruitment in Retrovirus Release," Proc. Natl. Acad. Sci., vol. 97, No. 24, pp. 13063-13068 (2000).
Szybalska, "Genetics of Human Cell Lines, IV. DNA-Mediated Heritable Transformation of a Biochemical Trait," Genetics: Szybalska and Szybalski, vol. 48, pp. 2026-2034 (1962).
Tabara, et al., "The rde-1 Gene, RNA Interference, and Transposon Silencing in C. Elegans," Cell, vol. 99, pp. 123-132 (1999).
Takeda, et al., "Construction of Chimaeric Processed Immunoglobulin Genes Containing Mouse Variable and Human Constant Region Sequences," Nature, vol. 314, pp. 452-454 (1985).
Tolstoshev, et al., "Gene Therapy, Concepts, Current Trails and Future Directions," Annu. Rev. Pharmacol. Toxicol., vol. 32, pp. 573-596 (1993).
Van Heeke, et al., "Expression of Human Asparagine Synthetase in *Escherichia coli**," The Journal of Biological Chemistry, vol. 264, No. 10, pp. 5503-5509 (1989).
VerPlank, et al., "Tsg101, a Homologue of Ubiquitin-Conjugating (E2) Enzymes, Binds the L Domain in HIV type 1 $Pr55^{Gag}$," Proc. Natl. Acad. Sci., vol. 98, No. 14, pp. 7724-7729 (2001).
Voller, et al., "Enzyme Immunoassays with Special Reference to ELISA Techniques," Journal of Clinical Pathology, vol. 31, pp. 507-520 (1978).
Wagner, et al., "Tsg101 is Essential for Cell Growth, Proliferation, and Cell Survival of Embryonic and Adult Tissues," Molecular and Cellular Biology, vol. 23, No. 1, pp. 150-162 (Jan. 2003).
Walsh, et al., "Gene Therapy for Human Hemoglobinopathies," Proceeding of the Society for Experimental Biology and Medicine, vol. 204, No. 3, pp. 289-300 (1993).
Wang, et al., "Dimerization of Zinc Fingers Mediated by Peptides Evolved in Vitro from Random Sequences," Proc. Natl. Acad. Sci. USA, vol. 96, pp. 9568-9573 (1999).
Ward, et al., "Binding Activities of a Repertoire of Single Immunoglobulin Variable Domains Secreted from *Escherichia coli*," Nature, vol. 341, pp. 544-546 (1989).
Whitlock, et al., "Long-Term Culture of B Lymphocytes and Their Precursors from Murine Bone Marrow," Proc. Natl. Acad. Sci. USA, vol. 79, pp. 3608-3612 (1982).
Wigler, et al., "Transfer of Purified Herpes Virus Thymidine Kinase Gene to Cultured Mouse Cells," Cell, vol. 11, pp. 223-232 (1977).
Wigler, et al., "Transformation of Mammalian Cells with an Amplifiable Dominant-Acting Gene," Proc. Natl. Acad. Sci. USA, vol. 77, No. 6, pp. 3567-3570 (1980).
Wills, et al., "Form, Function, and Use of Retroviral Gag Proteins," AIDS, vol. 5, No. 6, pp. 639-654 (1991).
Wills, et al., "An Assembly Domain of the Rous Sarcoma Virus Gag Protein Required Late in Budding," Journal of Virology, vol. 68, No. 10, pp. 6605-6618 (1994).
Wu, et al., "Receptor-Mediated in Vitro Gene Transformation by a Soluble DNA Carrier System," The Journal of Biological Chemistry, vol. 262, No. 10, pp. 4429-4432 (1987).
Wu, et al., "Delivery System for Gene Therapy," Biotherapy, vol. 3, pp. 87-95 (1991).
Yasuda, et al., "A Proline-Rich Motif (PPPY) in the Gag Polyprotein of Mason-Pfizer Monkey Virus Plays a Maturation-Independent Role in Virion Release," Journal of Virology, vol. 72, No. 5, pp. 4095-4103 (1998).
Yuan, et al., "Mutations Altering the Moloney Murine Leukemia Virus p12 Gag Protein Affect Virion Production and Early Events of the Virus Life Cycle," The EMBO Journal, vol. 18, No. 17, pp. 4700-4710 (1999).
Zamore, et al., "RNAi: Double-Stranded RNA Directs the ATP-Dependent Cleavage of mRNA at 21 to 23 Nucleotide Intervals," Cell, vol. 101, pp. 25-33 (2000).
Zhang, et al., "Synthetic Zinc Finger Transcription Factor Action at an Endogenous Chromosomal Site," The Journal of Biological Chemistry, vol. 275. No. 43, pp. 33850-33860 (2000).
Zaug, et al., "The Intervening Sequence RNA of Tetrahymena is an Enzyme," Science, vol. 231, pp. 470-475 (1986).
Zaug, et al., "The Tetrahymena Ribozyme Acts like an RNA Restriction Endonuclease," Nature, vol. 324, pp. 429-433 (1986).
Zaug, et al., "A Labile Phosphodiester Bond at the Ligation Junction in a Circular Intervening Sequence RNA," Science, vol. 224, pp. 574-578 (1984).
Zhong, et al., "Perturbation of TSG101 Protein Affects Cell Cycle Progression," Cancer Research, vol. 58, pp. 2699-2702 (1998).
Zijlstra, et al., "Germ-Line Transmission of a Disrupted $\beta_2$-microglobulin Gene Produced by Homologous Recombination in Embryonic Stem Cells," Nature, vol. 342, pp. 435-438 (1989).
Ausubel, et al., "Current Protocols in Molecular Biology," John Wiley & Sons, Inc., New York (1994).
Gait, "Oligonucleotide Synthesis, A Practical Approach," IRL Press, Oxford (1984).
Harlow, et al., "Antibodies: A Laboratory Manual," Cold Spring Harbor Laboratory (1988).
Ishikawa, et al., "Enzyme Immunoassay," Igaku-Shoin, Tokyo-New York (1981).
Kriegler, "Gene Transfer and Expression-A Laboratory Manual," Stockton Press (1990).
Maggio, "Enzyme-Immunoassay," CRC Press, Inc., Boca Raton, Florida (1980).
Friedmann, "Gene Therapy—A New Kind of Medicine," Tibtech, vol. 11, pp. 156-159 (1993).
Williamson, "From Genome Mapping to Gene Therapy," Tibtech, vol. II, pp. 159-161 (1993).
Mitani, et al., "Delivering Therapeutic Genes—Matching Approach and Application," Tibtech, vol. 11, pp. 162-166 (1993).
Dillon, "Regulating Gene Expression in Gene Therapy," Tibtech, vol. 11, pp. 167-173 (1993).
Porteous, et al., "How Relevant are Mouse Models for Human Disease to Somatic Gene Therapy?" Tibtech, vol. 11, pp. 173-181 (1993).
Dodet, "Commercial Prospects for Gene Therapy—A Company Survey," Tibtech, vol. 11, pp. 182-189 (1993).
Wivel, "Regulatory Considerations for Gene-Therapy Strategies and Products," Tibtech, vol. 11, pp. 189-192 (1993).
Friedmann, et al., "Gene Therapy for Disorders of the Nervous System," Tibtech, vol. II. pages 192-197 (1993).
Sikora, "Gene Therapy for Cancer," Tibtech, vol. II, pp. 197-201 (1993).
Findeis, et al., "Targeted Delivery of DNA for Gene Therapy via Receptors," Tibtech, vol. 11, pp. 202-205 (1993).
Dzau, et al., "Gene Therapy for Cardiovascular Disease," Tibtech, vol. 11, pp. 205-210 (1993).
Nabel, et al., "Direct Gene Transfer for Immunotherapy and Immunization," Tibtech, vol. 11, pp. 211-215 (1993).

* cited by examiner

| Vps28 Constructs | Interaction with Tsg101 | % of Inhibition |
|---|---|---|
| pVps28       1———————221 | + | 58.5% |
| pVps28ΔN1       28——————221 | + | 71.9% |
| pVps28ΔN       60————221 | − | 0% |
| pVps28Δ19   1  18———————221 | − | 0% |
| pVps28Δ127   1———125  168—221 | + | 62.7% |
| pVps28ΔC   1——————182 | + | 67.1% |

| | 1 | 2 | 3 | 4 | 5 |
|---|---|---|---|---|---|
| Control | 18.36 | 94.88 | 249.96 | 415.5 | 664.16 |
| hVps28&C2 | 0 | 11.5 | 28.92 | 93.82 | 218.74 |

METHOD FOR REDUCING HIV VIRAL BUDDING BY ADMINISTERING A VPS28-SPECFIC ANTIBODY THAT DISRUPTS GAG-TSG101-VPS28 BINDING INTERACTIONS

This application is a U.S. National Stage application, filed under 35 U.S.C. §371, based on International Application No. PCT/US2004/004518, filed Feb. 12, 2004, which claims the benefit under 35 U.S.C. §119(e) of U.S. Provisional Patent Application No. 60/446,909, filed on Feb. 12, 2003, both of which are incorporated by reference herein in their entirety.

1. FIELD OF THE INVENTION

The invention relates to method and composition for treatment of viral infections based on the interaction between mammalian VPS28 protein and TSG101 protein. The invention also relates to methods and compositions for treatment of viral infection by modulating the interaction between VPS28 protein and TSG101 protein and by modulating the expression and/or activity of VPS28. The invention also relates to TSG101-VPS28 interaction based methods and compositions for evaluation and screening of drug which can be used for treatment of viral infections. The invention further relates to compositions and methods of using VPS28 protein or peptides in evaluation and screening for drugs which can be used for treatment of viral infection.

2. BACKGROUND OF THE INVENTION

The final step in the assembly of an enveloped virus assembly requires separation of budding particles from the cellular membranes. Three distinct functional domains in Gag, i.e., PTAP in HIV-1 [SEQ ID NO.: 19](Gottlinger et al., 1991. Proc Natl Acad Sci USA 88, 3195-9; Huang et al., 1995, J Virol 69, 6810-8); PPPY in RSV [SEQ ID NO.: 20] (Parent et al. 1995, J Virol 69, 5455-60), MuLV (Yuan et al., 1999, Embo J 18, 4700-10), and M-PMV (Yasuda et al., 1998, J Virol 72, 4095-103); and YXXL in EIAV [SEQ ID NO.: 21] (Puffer et al., 1997, J Virol 71, 6541-6), have been identified in different retroviruses that are required for this function and have been termed late, or L domains (Wills et al., 1991, Aids 5, 639-54). In HIV-1, the L domain contains a PTAP motif and is required for efficient HIV-1 release (see, e.g., Wills et al., 1994, J. Virol. 68, 6605-6618; Gottlinger et al., 1991, Proc. Natl. Acad. Sci. USA 88, 3195-3199; Huang et al., 1995, J. Virol. 69, 6810-6818). The L domain of HIV-1 p6, especially the PTAP motif, binds to the cellular protein TSG101 and recruits it to the site of virus assembly to promote virus budding (VerPlank et al., 2001, Proc. Natl. Acad. Sci. USA 98:7724-7729; Garrus et al., 2001, Cell 107:55-65; Martin-Serrano et. al., 2001, Nature Medicine 7:1313-19; Pornillos et al., 2002, EMBO J. 21:2397-2406; Demirov et al., 2002, Proc. Natl. Acad. Sci. USA 99:955-960; PCT Publication WO 02/072790; U.S. Patent Application Publication No. US 2002/0177207). The UEV domain of TSG101 binds the PTAP motif and mono-ubiquitin (Pornillos et al., 2002, Embo J 21, 2397-406; Pornillos et al., 2002, Nat Struct Biol 9, 812-7), which has also been implicated in HIV-1 budding (Patnaik et al., 2000, Proc Natl Acad Sci USA 97, 13069-74; Schubert et al., 2000, Proc Natl Acad Sci USA 97, 13057-62; Strack et al., 2000, Proc Natl Acad Sci USA 97, 13063-8). Depletion of cellular TSG101 (Garrus et al., 2001, Cell 107:55-65) or over-expression of a truncated form of TSG101 inhibits HIV-1 release (Demirov et al., 2002, Proc. Natl. Acad. Sci. USA 99:955-960). Under certain circumstances, TSG101 can even substitute for the HIV-1 L domain to promote virus release (Martin-Serrano et. al., 2001, Nature Medicine 7:1313-19). Antibodies targeting TSG101 have been shown to inhibit viral release (Li, U.S. Provisional Patent Application No. 60/425,299, filed Oct. 1, 2002).

TSG101 plays important roles in cell growth (Zhong et al., 1998, *Cancer Res* 58, 2699-702; Oh et al., 2002, *Proc Natl Acad Sci USA* 99, 5430-5; Krempler et al., 2002, *J Biol Chem* 277, 43216-23; Wagner et al., 2003, *Mol Cell Biol* 23, 150-62; Li et al., 1996, *Cell* 85, 319-29), cellular protein trafficking (Babst et al., 2000, *Traffic* 1, 248-58; Bishop et al., 2002, *J Cell Biol* 157, 91-101), and degradation of p53 (Li et al., 2001, *Proc Natl Acad Sci USA* 98, 1619-24; Ruland et al., 2001, *Proc Natl Acad Sci USA* 98, 1859-64; Moyret-Lalle et al., 2001, *Cancer Res* 61, 486-8). In yeast, the Tsg101 ortholog Vps23 has been shown to interact with Vps28 and Vps37 and to form a protein complex named ESCRT-I, which is critical for endosomal protein sorting into the multivesicular body pathway (Katzmann et al., 2001, *Cell* 106, 145-55). It is hypothesized that this intracellular multivesicular body formation resembles HIV-1 release at the plasma membrane (Garrus et al., 2001, Cell 107:55-65; Patnaik et al., 2000, *Proc Natl Acad Sci USA* 97, 13069-74). In mammalian cells, TSG101 interacts with Vps28 to form an ESCRT-I-like complex (Babst et al., 2000, *Traffic* 1, 248-58; Bishop et al., 2002, *J Cell Biol* 157, 91-101; Bishop et al., 2001, *J Biol Chem* 276, 11735-42), although the mammalian homolog of Vps37 has not been identified.

Citation of references herein shall not be construed as an admission that such references are prior art to the present invention.

3. SUMMARY OF THE INVENTION

The invention provides methods and compositions for treatment of viral infections, including HIV infection. The invention provides a method of inhibiting or reducing viral release thereby treating viral infection in an animal, e.g., a human, by modulating, e.g., interfering with, TSG101-VPS28 interaction. This can be achieved, for example, by administering an agent, such as but is not limited to a peptide or polypeptide, an antibody, and a small molecule, which binds to TSG101 or VPS28 such that the binding inhibits or reduces the binding of TSG101 to VPS28 or disrupts TSG101-VPS28 protein complexes. The invention also provides a method of inhibiting or reducing viral release thereby treating viral infection in an animal, e.g., a human, by modulating the expression of tsg101 or vps28 gene. This can be achieved, for example, by using siRNA targeting the tsg101 and/or vps28 gene. The invention also provides a method of inhibiting or reducing viral release thereby treating viral infection in an animal, e.g., a human, by modulating, e.g., interfering with, the interaction of VPS28 to a protein which binds to the C-terminal region of the VPS28 protein during viral assembly and budding process. This can be achieved, for example, by administering an agent, such as but is not limited to a peptide or polypeptide, an antibody, and a small molecule, which binds to VPS28 such that the binding inhibits or reduces the binding of VPS28 to such a protein or disrupts protein complexes formed between VPS28 and such protein.

The invention also encompasses any molecules that can be used to modulate TSG101-VPS28 interaction and the interaction between VPS28 and a protein which binds to the C-terminal region of the VPS28 protein during viral assembly and budding process; and molecules that can be used to modulate the expression of tsg101 and/or vps28 gene.

The present invention also provides methods for identifying molecules that can be used to modulate TSG101-VPS28 interaction and the interaction between VPS28 and a protein which binds to the C-terminal region of the VPS28 protein during viral assembly and budding process; and molecules that can be used to modulate the expression of tsg101 and/or vps28 gene. For example, TSG101-VPS28 protein complexes may be used to screen for agents which disrupts such complexes.

4. BRIEF DESCRIPTION OF THE FIGURES

Figure 1B:
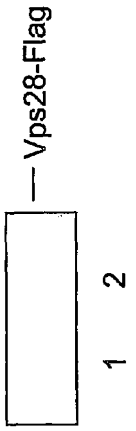
Figure 1C:
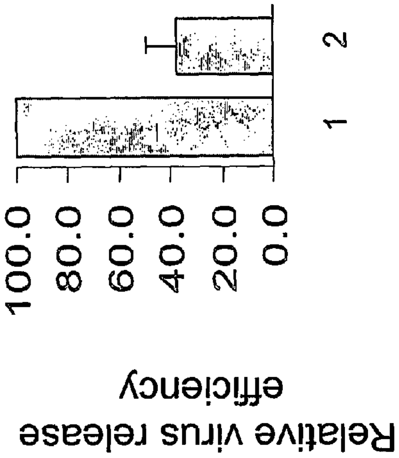

FIGS. 1A-1C depict results demonstrating that Vps28 is required for HIV-1 release from 293T cells. FIG. 1A. Analysis of HIV-1 release by Western blotting. The effect of shRNA targeting Vps28 on HIV-1 release was studied by co-transfection of pNL4-3 with pU6-Vps28 or the control vector pGEM-U6 in 293T cells. Lane 1, 4: 293T cells; lane 2, 5: pNL4-3+pGEM-U6; lane 3, 6: pNL4-3+pU6-hVps28. Cell and viral lysates were prepared as described in Materials and Methods in Section 6, infra. HIV-1-specific proteins were detected with a p24 Mab. FIG. 1B. Effect of pU6-hVps28 on Vps28 expression in transfected 293T cells. Cell lysates from 293T cells transfected with pFlag-hVps28+pGEM U6 (lane 1) or pFlag-hVps28+pU6-hVps28 were analyzed by Western blotting using an anti-Flag mAb to detect the expression of Flag-tagged Vps28. FIG. 1C. Quantitative analysis of the effect of depletion of hVps28 on the production of virion associated Gag. Relative virus release efficiency was calculated as the amount of virion-associated p24 as a fraction of the total Gag (cell-associated Pr55Gag+p41Gag+p24+virion p24), as described in Materials and Methods in Section 6, infra.

Figures 2A, 2B:
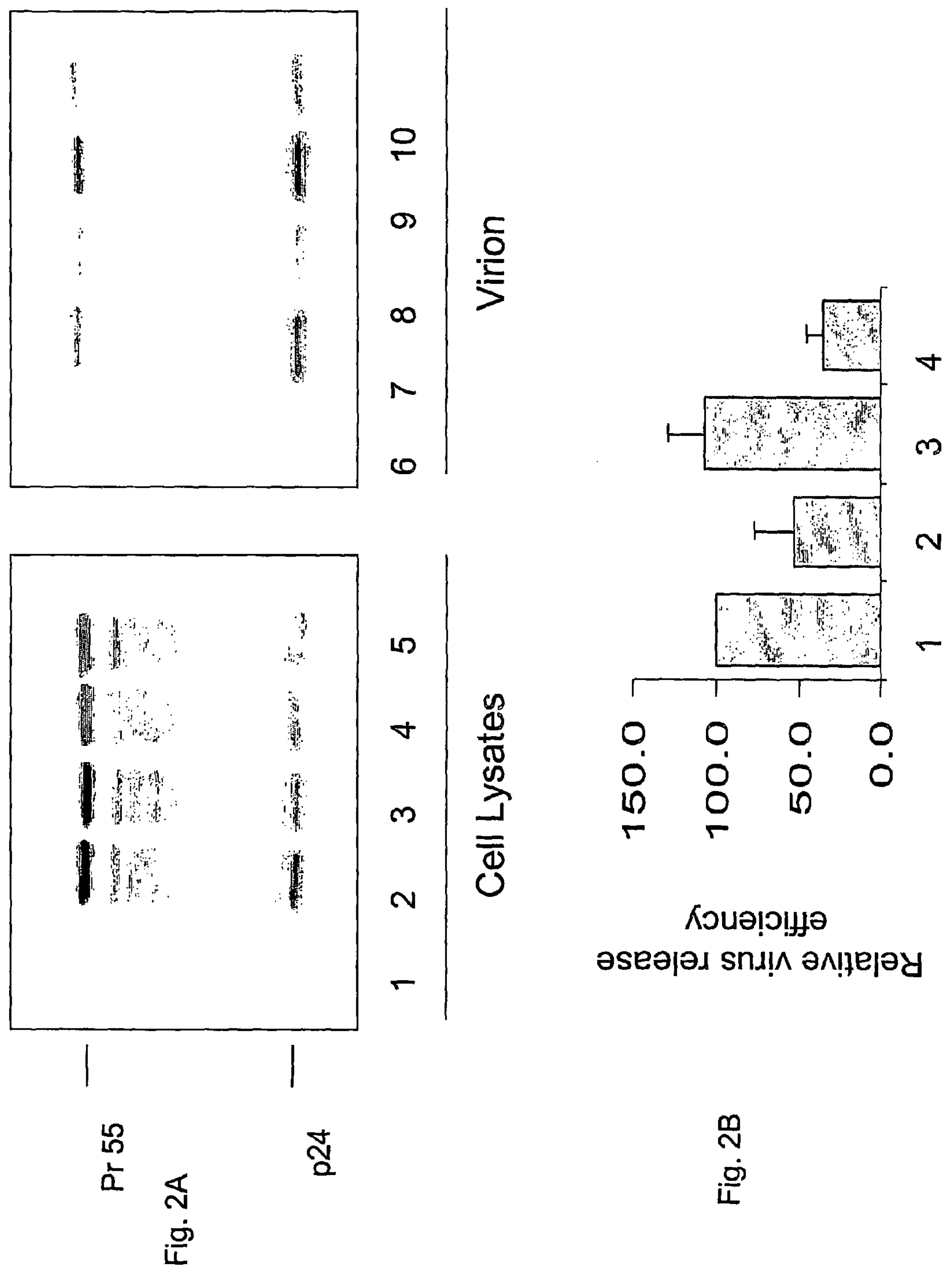
Figure 2C:
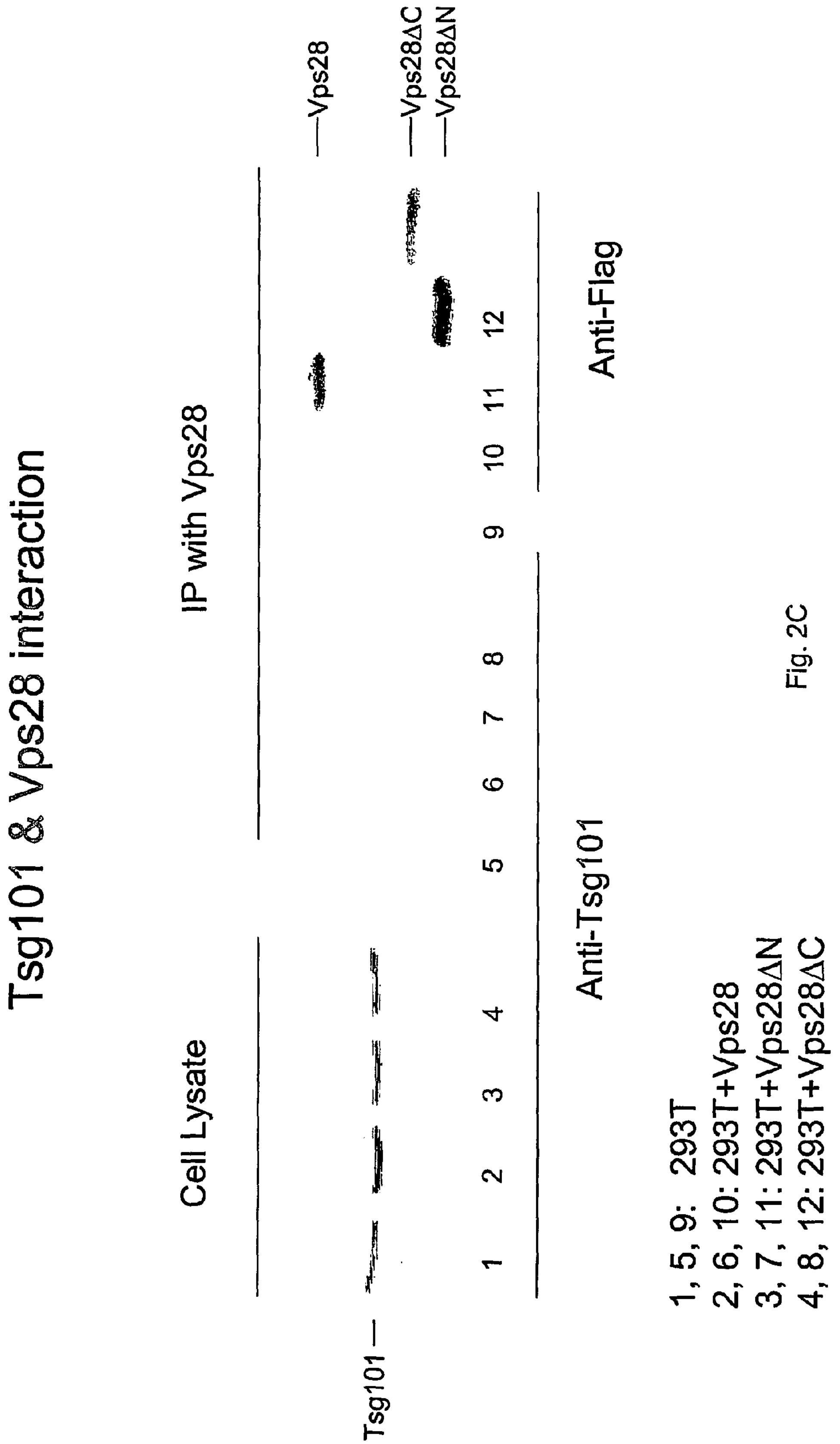

FIG. 2A. Vps28 mutants inhibit HIV-1 release. 293T cells were co-transfected with pNL4-3 and the pVps28 or Vps28 mutant construct. Cell (lanes 1 to 5) and viral (lanes 6 to 10) lysates were prepared as described in Materials and Methods in Section 6, infra. HIV-1-specific proteins were detected with the p24 Mab. Lanes 1 and 6, 293T; lanes 2 and 7, pNL4-3+control vector; lanes 3 and 8, pNL4-3+pVps28; lanes 4 and 9, pNL4-3+pVps28ΔN; lanes 5 and 10, pNL4-3+pVps28ΔC. FIG. 2B. Quantitative analysis of the effect of Vps28 mutant on HIV-1 release. Relative virus release efficiency was calculated as described in the Materials and Methods in Section 6, infra. Data are averages from three independent experiments, SE. FIG. 2C. Tsg101 co-immunoprecipitates with hVps28. 293T cells were transfected with pVps28, pVps28ΔN, or pVps28ΔC. At 2 days post-transfection, cell lysates were prepared and subjected to immunoprecipitation with the anti-Flag Mab conjugated to beads. Tsg101 expression in all transfected cells were not significantly altered. Lane 1, 293T; lane 2, 293T plus pVps28; lane 3, 293T plus pVps28ΔN; lane 4, 293T plus pVps28ΔC. Tsg101 was precipitated from cells transfected with pVps28 (lane 6) and pVps28ΔC (lane 8) but not from 293T cells (lane 5) or cells transfected with pVps28ΔN (lane 7). Vps28 and its mutant forms were precipitated by the anti-Flag Mab (lanes 10-12).

Figure 3:
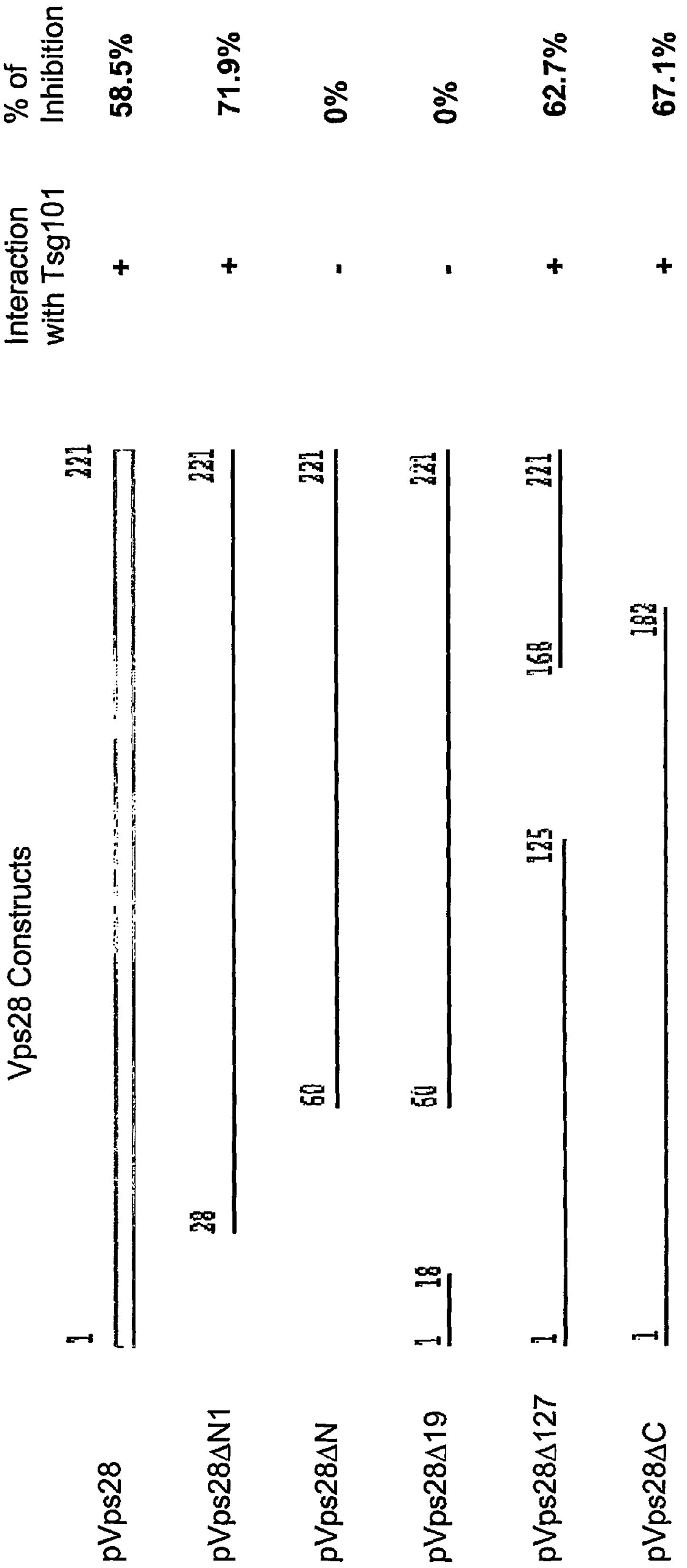

FIG. 3 Identification of regions of Vps28 important for the inhibition of HIV-1 release and interaction with Tsg101. Vps28 mutants were constructed and analyzed for interaction with Tsg101 and inhibition of HIV-1 release as described in Materials and Methods in Section 6, infra, and in FIG. 2. Interaction with Tsg101 is indicated as + or −. +, detection of Tsg101 after immunoprecipitation with Vps28; −, no detection of Tsg101 after immunoprecipitation with Vps28.

Figure 4:
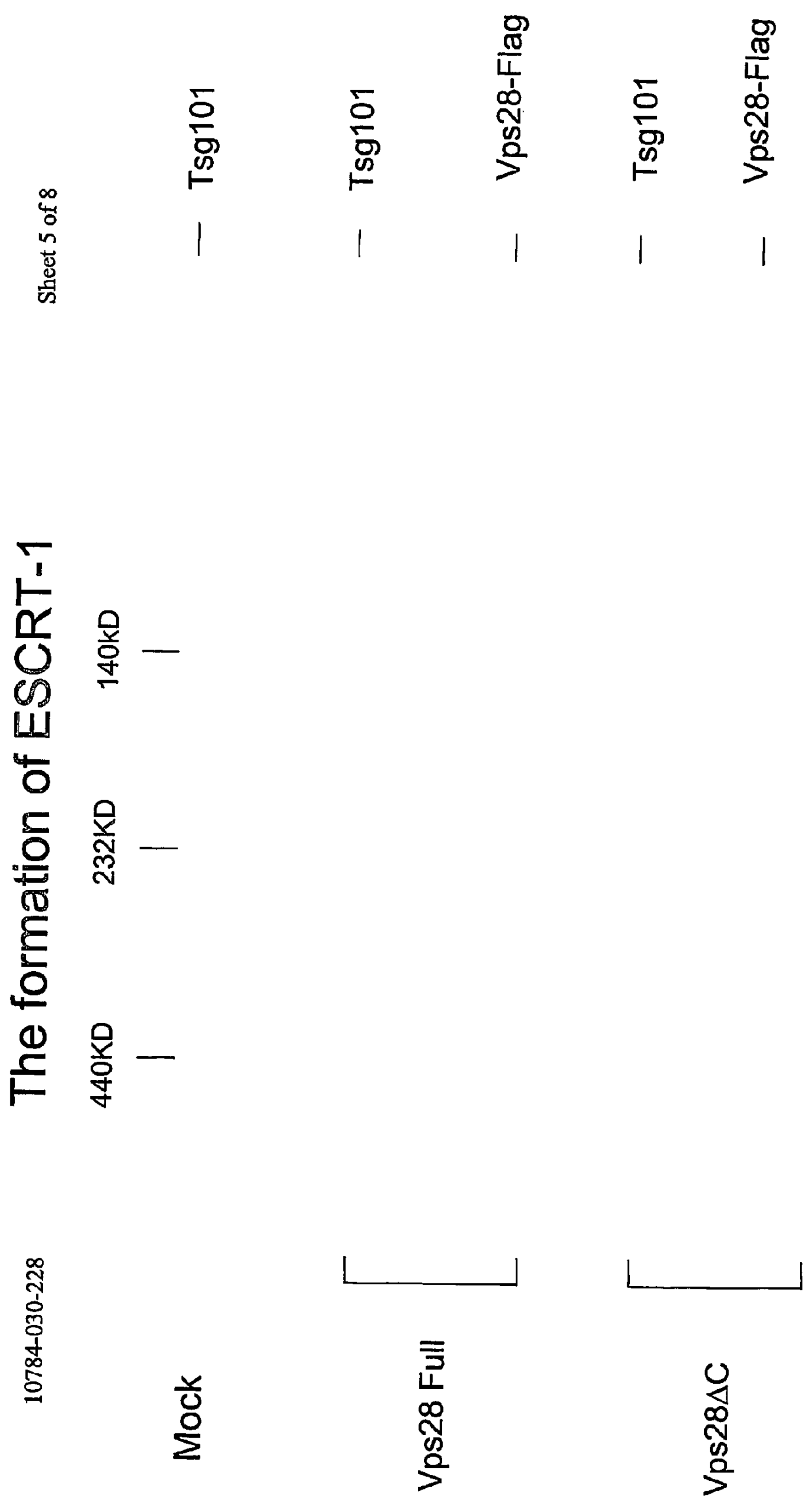

FIG. 4. Characterization of the ESCRT-1-like complex. Gel filtration analysis of cell extracts from 293T cells or 293T cell transfected with pVps28 or pVps28ΔC. The column fractions were analyzed by Western blotting using anti-Tsg101 and anti-Flag antibodies.

Figure 5A:
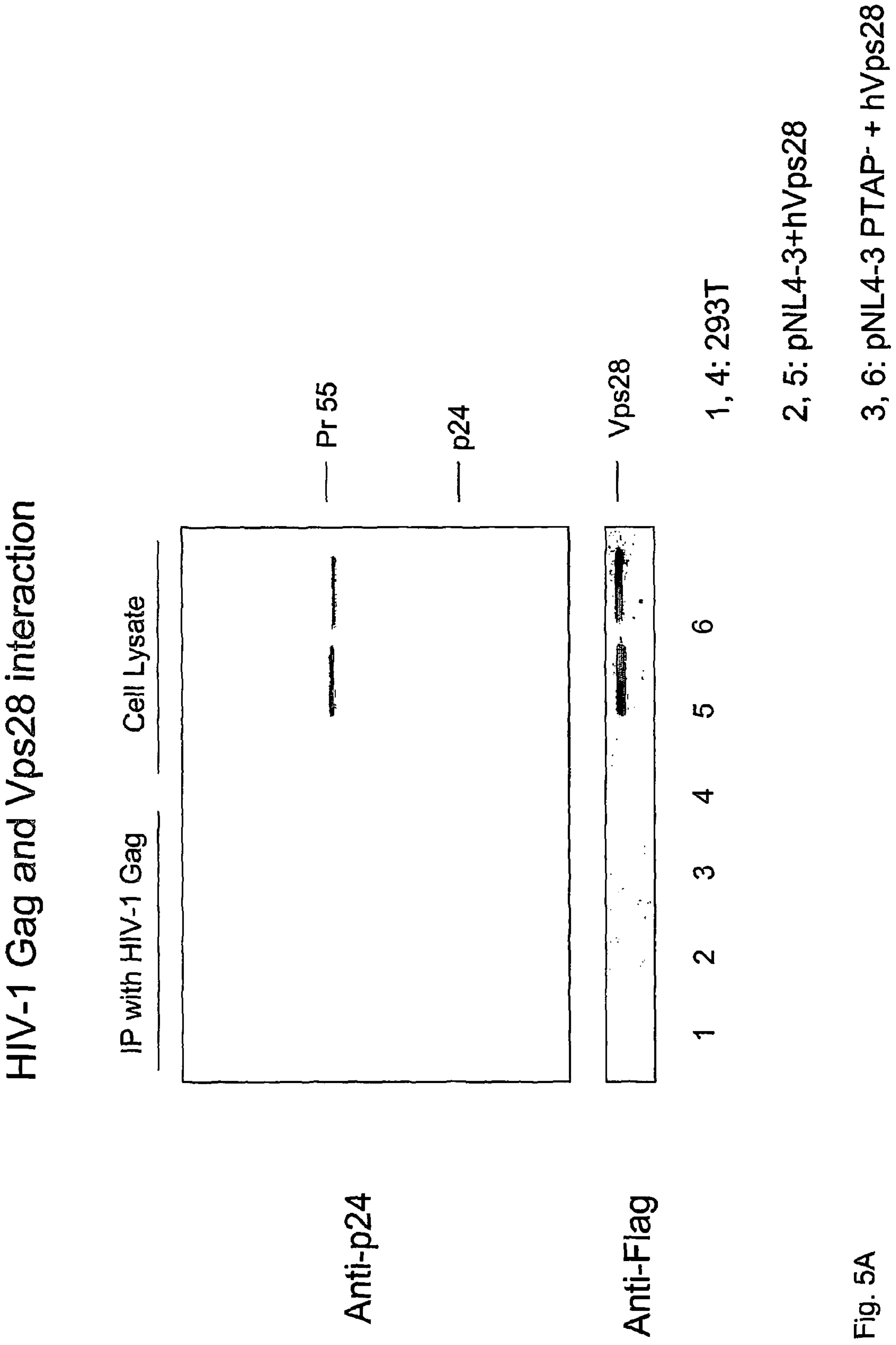
Figure 5B:
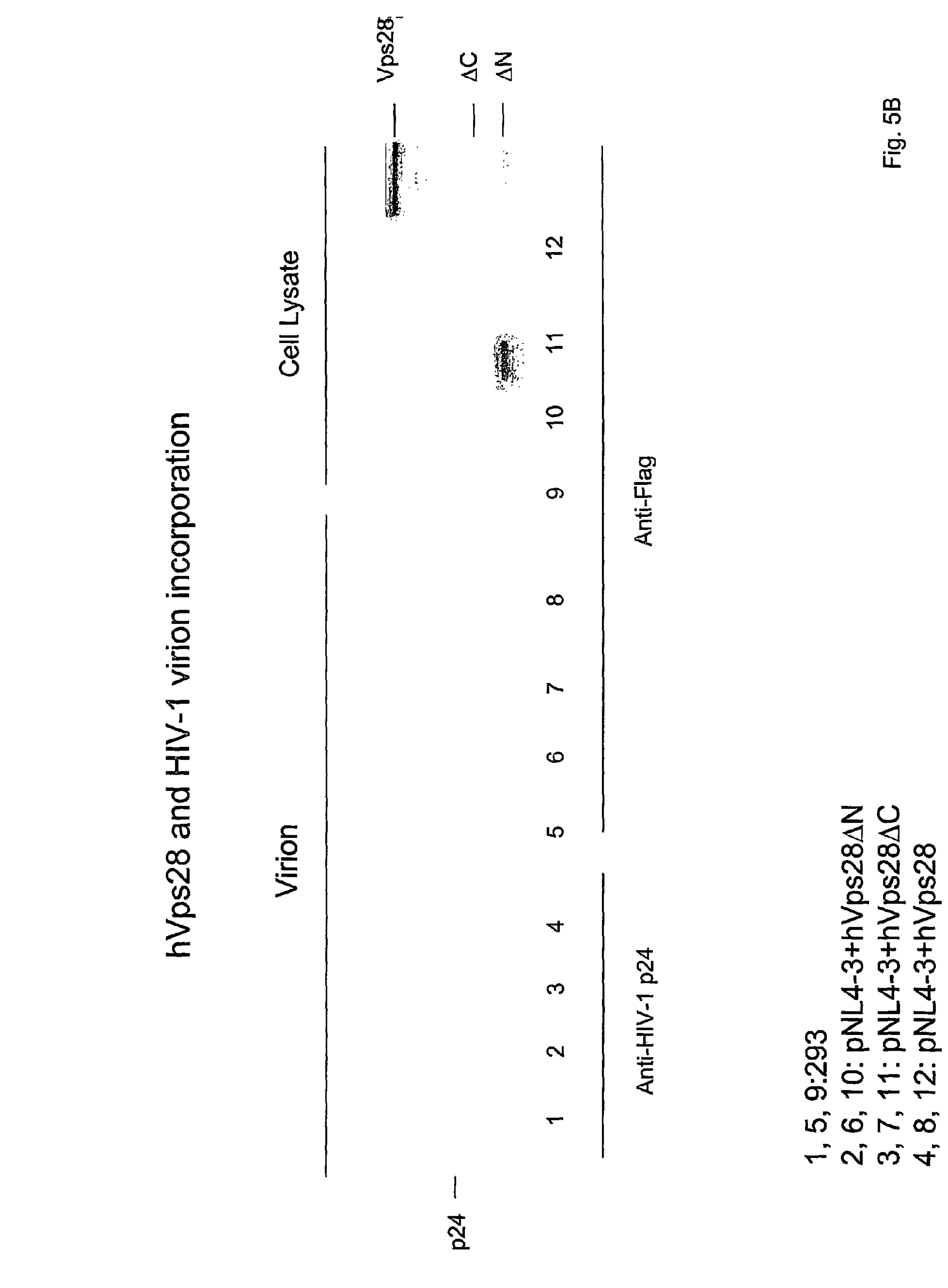

FIG. 5A. HIV-1 Gag co-immunoprecipitates with hVps28. 293T cells were co-transfected with pNL4-3+pFlag-hVps28 and pNL4-3 PTAP-+pFlag-hVps28, and their cell lysates were subjected to co-immunoprecipitation with anti-HIV-1 p7 antibody. Western blot of the cell lysate and immunoprecipitation products stained with anti-p24 and M2 anti-Flag mAbs. Lanes 1 and 4, 293 cells; lanes 2 and 5, cells transfected with pNL4-3+pFlag-hVps28; lanes 3 and 6, cells transfected with pNL4-3 PTAP-+pFlag-hVps28. FIG. 5B. Vps28 is incorporated into HIV-1 virions. 293T cells were co-transfected with pNL4-3 and pFlag-Vps28, pFlag-Vps28ΔN, or pFlag-hVps28ΔC. After the amount of virions was normalized by Western blotting of HIV-1 virions using anti-p24 mAb (a), the amount of hVps28 and mutants incorporated into HIV-1 virions were compared by Western blotting using M2 anti-Flag mAb (b). (c). Western blot analysis of cell lysates using M2 anti-Flag mAb. Lanes 1, 5, and 9, 293 mock-transfected cells; lanes 2, 6, and 10, pNL4-3+pFlag-Vps28ΔN-transfected cells; lanes 3, 7, and 11, pNL4-3+pFlag-hVps28ΔC-transfected cells; lanes 4, 8, and 12: pNL4-3+pFlag-hVps28-transfected cells.

Figure 6:
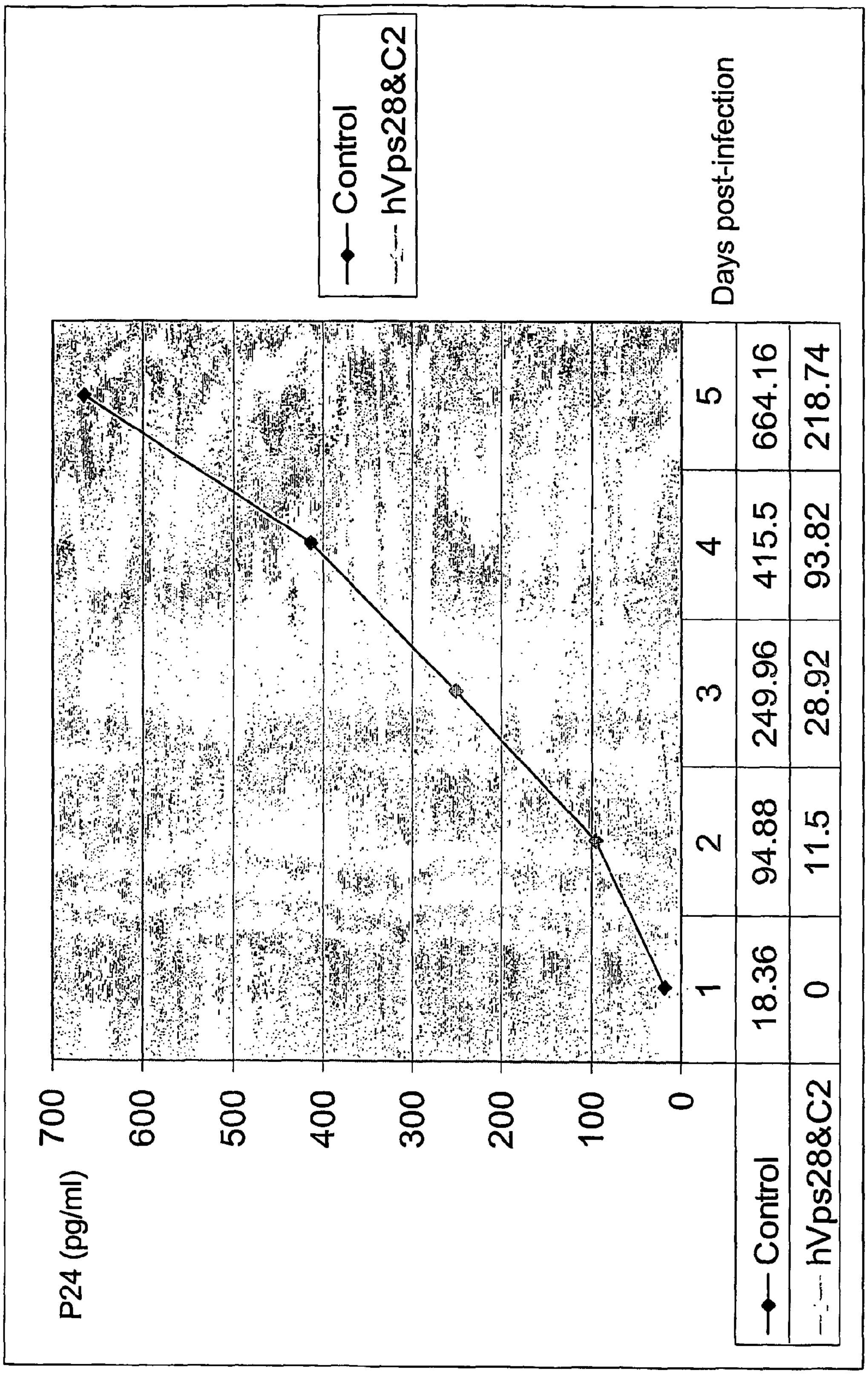

FIG. 6. HIV-1 replication is inhibited by the expression of hVps28ΔC in CD4+ T cells. Jurkat cells were transduced with an M-MuLV-derived retroviral expression vector expressing Vps28ΔC or with Lac Z as a control. HIV-1 replication was monitored in the transduced cells by measuring p24 in the supernatant.

5. DETAILED DESCRIPTION OF THE INVENTION

The invention provides methods and compositions for treatment of viral infections, including HIV infection. The methods and compositions of the invention are based, at least in part, on the inventors' discovery that Vps28 is important to the release of enveloped viruses (viral budding), and that the involvement of VPS28 in viral release is through VPS28-TSG101 interaction. In particular, the inventors have discovered that reducing intracellular Vps28 expression by gene silencing with short hairpin RNA (shRNA) inhibited HIV-1 release. Over-expression of mutants of Vps28 also inhibited HIV-1 release. Vps28 was co-immunoprecipitated with the wild-type Gag but not with L domain mutant Gag molecules in virus-expressing cells. A small N-terminal region of Vps28 (amino acids 28-59) is identified as being critical to interaction with Tsg101 and to their ability to inhibit HIV-1 release. Vps28 mutants that inhibit HIV-1 release also disrupted ESCRT-I like complex formation. Expression of mutant Vps28 inhibit HIV-1 replication in CD4+ T cells, indicating that Vps28 and Vps28-Tsg101 protein complexes are targets for the design of anti-viral inhibitors. The invention thus provides a method of inhibiting or reducing viral release thereby treating viral infection in an animal, e.g., a human, by modulating, e.g., interfering with, TSG101-VPS28 interaction. This can be achieved, for example, by administering an agent, such as but is not limited to a peptide or polypeptide, an antibody, and a small molecule which binds to TSG101 or VPS28 such that the binding inhibits or reduces the binding of TSG101 to VPS28 or disrupts TSG101-VPS28 protein complexes. In a preferred embodiment, the administered agent comprising a fragment of a VPS28 protein comprising amino acids 28 to 59 of a VPS28 protein, or a functional derivative thereof. The invention also provides a method of inhibiting or reducing viral release thereby treating viral infection in an animal, e.g., a human, by modulating the expression of tsg101 or vps28 gene. This can be achieved, for example, by using siRNA targeting the tsg101 and/or vps28 gene. The invention also provides a method of inhibiting or reducing viral release thereby treating viral infection in an animal, e.g., a human, by modulating, e.g., interfering with, the interaction of VPS28 to other protein which binds to the C-terminal region of the VPS28 protein during viral assembly and budding process. This can be achieved, for example, by administering an agent, such as but is not limited to a peptide or polypeptide, an antibody, and a small molecule, which binds to VPS28 such that the binding inhibits or reduces the binding of VPS28 to such a protein or disrupts protein complexes formed between VPS28 and such protein.

The invention also encompasses any molecules that can be used to modulate TSG101-VPS28 interaction and the interaction between VPS28 and a protein which binds to the C-terminal region of the VPS28 protein during viral assembly and budding process; and any molecules that can be used to modulate the expression of tsg101 and/or vps28 gene.

The present invention also provides methods for identifying any molecules that can be used to modulate TSG101-VPS28 interaction and the interaction between VPS28 and a protein which binds to the C-terminal region of the VPS28 protein during viral assembly and budding process; and any molecules that can be used to modulate the expression of tsg101 and/or vps28 gene. For example, TSG101-VPS28 protein complexes may be used to screen for agents which disrupts such complexes.

5.1. VPS28 is Involved in Viral Release

Vps28 is demonstrated to be important for HIV-1 release. In one embodiment, a DNA-based strategy (shRNA) is used for the delivery of siRNA (Paddison et al., 2002, *Genes Dev* 16, 948-58) against Vps28 to determined its effect on HIV-1 release in transfected 293T cells. For this purpose, a DNA vector (pU6-Vps28) containing the U6 promoter and siRNA-generating sequences targeting nucleotides 359 to 386 of the Vps28 coding region is constructed. As shown in FIG. 1, co-transfection of pNL4-3 with pU6-Vps28 or the control vector pGEM-U6 does not affect HIV-1 expression in transfected 293T cells (FIG. 1A, lanes 2 and 3). Co-transfection of pNL4-3 with pU6-Vps28 inhibits HIV-1 release by 66% (lane 6) when compared to co-transfection with pGEM-U6 (lane 5). Targeting of the shRNA to the Vps28 coding region reduces the expression of Vps28 by approximately 80% (FIG. 1B, lane 2) when compared to the control vector (FIG. 1B, lane 1). In repeated experiments, a 50-72% inhibition of HIV-1 release using the shRNA targeting Vps28 (FIG. 1C) is observed. Certain Vps28 mutants are demonstrated to block HIV-1 release. In the disclosure, the term "mutant" and "polypeptide" and "fragment" are used interchangeably. In one embodiment, as an initial step in screening for Vps28 mutants that may inhibit HIV-1 release, an N-terminal 59-amino acid deletion mutant (Vps28ΔN) and a C-terminal 43-amino acid deletion mutant (Vps28ΔC) of Vps28 are constructed. Both constructs express Vps28 proteins fused with a Flag epitope tag at the C-terminus for easy detection. The effect of the N-terminal and C-terminal deletion mutants of Vps28 on HIV-1 release is studied in transfected 293T cells. Expression of the C-terminal deletion mutant (Vps28ΔC) reduces the release of HIV-1 by 67% (FIG. 2A, lane 10) when compared to the control vector (FIG. 2A, lane 7). On the other hand, expression of the N-terminal deletion mutant (Vps28ΔN) has little effect on the release of HIV-1 (FIG. 2A, lane 9). Expression of exogenous full-length Vps28 has a moderate effect (58% reduction) on the release of HIV-1 (FIG. 2A, lane 8). In repeated experiments, Vps28ΔC inhibits HIV-1 release by 53-75% (FIG. 2B).

In another embodiment, the interaction of these mutants with TSG101 is also evaluated. Both mutants, as well as the full-length Vps28, are immunoprecipitated from transfected 293T cells by the anti-Flag antibody. TSG101 is co-precipitated with the full-length Vps28 (FIG. 2C, lane 6). Deletion of C-terminal 43 amino acids of Vps28 has no significant effect on its interaction with TSG101 (FIG. 2C, lane 8). However, deletion of the N-terminal 52 amino acids from Vps28 significantly reduces its interaction with TSG101 (FIG. 2C, lane 7), despite the mutant protein is efficiently precipitated (FIG. 2C, lane 11). Expression of exogenous full length or mutant Vps28 shows no significant effect on the expression of TSG101 in transfected 293T cells (FIG. 2C, lanes 1 to 4).

To further identify the region of Vps28 that is important for its interaction with Tsg101 and for the inhibition of virus release, several more Vps28 mutant constructs are evaluated. Deletion of the N-terminal 27 amino acids does not significantly affect its interaction with Tsg101, and expression of this protein reduces HIV-1 release by about 72% (FIG. 3). Internal deletion of amino acids 19 to 59 abolishes Vps28 interaction with Tsg101, and this mutant does not affect HIV-1 release (FIG. 3). Deletion of another C-terminal region (amino acids 126 to 167) of Vps28 also does not affect its interaction with Tsg101 and this mutant inhibits HIV-1 release by about 63% (FIG. 3). These results indicate that the N-terminal region of Vps28, and especially amino acids 28 to 59, plays an important role in the interaction with Tsg101, whereas the C-terminal half of Vps28 apparently does not. Mutant Vps28s that interacted with Tsg101 inhibited HIV-1 release, whereas mutant Vps28s that fail to interact with Tsg101 do not inhibit HIV-1 release.

In still another embodiment, the effect of Vps28 mutation on ESCRT-I-like complex formation is determined. To study the effect of Vps28 mutation on the formation of an ESCRT-I-like complex, cell extracts from pVps28ΔC- and pVps28-transfected cells and from control vector-transfected 293T cells are prepared and analyzed by size exclusion chromatography. Tsg101 migrates as a single species with an estimated molecular mass of 350 kDa in the control vector-transfected cells (FIG. 4). However, Tsg101 displays an additional smaller peak (about 200 kDa) in cells transfected with Vps28ΔC (FIG. 4). Similar results are also observed in pVps28-transfected cells (FIG. 4). It has been reported that over-expression of a myc-tagged Vps28 also disrupts ESCRT-I-like complexes (Bishop et al., 2002, *J Cell Biol* 157, 91-101). These results indicates that expression of Vps28ΔC or exogenous Vps28 disrupts some of the ESCRT-I-like complexes, and this disruption contributed to the observed inhibition of HIV-1 release.

In still another embodiment, interactions of Vps28 with HIV-1 Gag is determined. In yeast, Vps28 and TSG101 form a functional ESCRT-I-like complex that is critical for the sorting of vesicular proteins (Katzmann et al., 2001, *Cell* 106, 145-55; Bishop et al., 2001, *J Biol Chem* 276, 11735-42) The data reported above suggest that Vps28 and its interaction with TSG101 are important for HIV-1 release. Vps28 is recruited to the site of virus assembly through its interaction with TSG101. To test this, co-immunoprecipitation experiments are performed. A Vps28 expression vector (pVps28) is co-transfected with pNL4-3 or the PTAP-mutant (Huang et al., 1995, *J Virol* 69, 6810-8). Two days after transfection, cell lysates are immunoprecipitated with a goat anti-p7$^{Gag}$ antiserum, and the precipitated materials are analyzed by Western blot using anti-Flag antibody to detect the Flag-tagged Vps28. Both the wild-type Gag and PTAP-mutant Gag molecules are precipitated by the anti $p7^{Gag}$ antiserum (FIG. 5A, lanes 2 and 3). Flag epitope-tagged Vps28 is detected in the pNL4-3 cell lysates immunoprecipitated by the anti $p7^{Gag}$ antiserum (FIG. 5A, lane 2) but not in the PTAP-mutant cell lysates (FIG. 5A, lane 3). Comparable Flag-tagged Vps28 molecules are detected in both pNL4-3 cell lysates and PTAP-mutant cell lysates (FIG. 5A, lanes 5 and 6).

In still another embodiment, Vps28 is shown to be incorporated into HIV-1. It is observed that Vps28 is co-precipitated with HIV-1 Gag (FIG. 5A) interaction with TSG101. To determine whether the interaction between HIV-1 Gag and the ESCRT-I-like complex occurs only transiently during virus budding, and the complex is subsequently removed from released virions, or that some components of the ESCRT-I-like complex are incorporated into HIV-1 virions, full-length Vps28 and the N-terminal (Vps28ΔN) or C-terminal (Vps28ΔC) deletion mutants of Vps28 with pNL4-3 are co-expressed. Virions are collected and adjusted to contain comparable levels of p24. Both the full-length form and the C-terminal deletion mutant of Vps28 are detected in the released HIV-1 virions (FIG. 5B, lanes 7 and 8). However, the N-terminal deletion mutant of Vps28 is not detected in the released virions (lane 6), despite the fact that the intracellular expression level of the N-terminal deletion mutant of Vps28 (lane 10) is higher than those of full-length Vps28 (lane 12) or the C-terminal deletion mutant of Vps28 (lane 11).

In still another embodiment, certain Vps28 mutants are shown to inhibit HIV-1 replication in T cells. To test whether the functional interaction between HIV-1 Gag and TSG101/Vps28 could be a vulnerable target during HIV-1 replication, Jurkat (CD4+) cells are transduced with a retroviral expression vector expressing Vps28ΔC or with a control vector. They are then infected with HIV-1MN. Viral replication is monitored by measuring the secretion of p24 into the supernatants of infected cells from day 1 to day 5. HIV-1 replication in control vector-transduced Jurkat cells is first detected at day 1 after infection and found to increase thereafter (FIG. 5). No HIV-1 replication is detected in Vps28ΔC-transduced Jurkat cells on day 1 (FIG. 5). From day 2 to day 5, HIV-1 replication in Vps28ΔC-transduced Jurkat cells is reduced by 67% to 88% when compared to that in control Jurkat cells (FIG. 5).

5.1.1. TSG101 and VPS28 Polypeptides

The present invention provides TSG101 and VPS28 fragments for inhibiting viral budding. In embodiments of the invention, TSG101 or VPS28 fragments are used to interfere with the interaction between TSG101 and VPS28. The nucleic acid sequence of Tsg101 gene and the amino acid sequence of the encoded TSG101 protein is deposited as GenBank™ Accession Number U82130, which is incorporated herein by reference in its entirety. The nucleic acid sequence of the human Vps28 gene and the amino acid sequence of the encoded VPS28 protein is deposited as GenBank™ Accession Number NM016208 and is described in Bishop et al., 2001, *J Biol Chem* 276, 11735-42, which is incorporated herein by reference in its entirety.

5.1.1.1. TSG101 Polypeptides

The invention provides fragments of a TSG101 protein which can be used to modulate the interaction between TSG101 and VPS28. The TSG101 protein fragment or polypeptide can be prepared by standard method known in the art. In a preferred embodiment, the invention provides a fragment of a TSG101 protein which binds VPS28. In one embodiment, the invention provides a fragment of a TSG101 protein not comprising the UEV domain of a TSG101 protein. In a specific embodiment, the invention provides a fragment of a human TSG101 protein, or its murine homolog, not comprising the UEV domain. In another embodiment, the invention provides a fragment of a TSG101 protein comprising the coiled-coil domain of a TSG101 protein. In still another embodiment, the invention provides a fragment of a TSG101 protein comprising C-terminal domain of a TSG101 protein. The invention also provides any sequence that is at least 30%, 50%, 70%, 90%, or 95% homologous such fragments of a TSG101 protein. In some embodiments of the invention, the TSG101 protein fragments or polypeptides are at least 5, 10, 20, 50, 100 amino acids in length. The TSG101 fragments can be used to interfere with the binding a TSG101 protein with a VPS28 protein.

The invention also provides fragment of a TSG101 protein which is functionally equivalent to any TSG101 fragment described above. Such an equivalent TSG101 fragment may contain deletions, additions or substitutions of amino acid residues within the amino acid sequence encoded by the TSG101 protein gene sequences encoding the TSG101 protein but which result in a silent change, thus producing a functionally equivalent TSG101 protein fragment. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein fragment capable of exhibiting a substantially similar in vivo activity as the endogenous TSG101 protein fragment.

The TSG101 peptide fragments of the invention may be produced by recombinant DNA technology using techniques well known in the art. Thus, methods for preparing the TSG101 polypeptides and peptides of the invention by expressing nucleic acid containing TSG101 gene sequences encoding the TSG101 polypeptide or peptide. Methods which are well known to those skilled in the art can be used to construct expression vectors containing TSG101 polypeptide coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding TSG101 polypeptide sequences may be chemically synthesized using, for example, synthesizers. See, for example, the techniques described in "Oligonucleotide Synthesis", 1984, Gait, M. J. ed., IRL Press, Oxford, which is incorporated herein by reference in its entirety.

The invention also provides portions of a tsg101 gene for use for producing any TSG101 protein fragment of the invention described above. In a preferred embodiment, the invention provides a fragment of a tsg101 gene comprising the nucleotide region encoding a fragment not comprising the UEV domain of a TSG101 protein. In a specific embodiment, the fragment of a TSG101 gene is a fragment of a human tsg101 gene, or its murine homolog. The invention also provides any sequence that is at least 30%, 50%, 70%, 90%, or 95% homologous to such fragments of a tsg101 gene. In some embodiments of the invention, the fragment of a tsg101 gene is at least 20, 25, 40, 60, 80, 100, 500, 1000 bases in length. Such sequences may be useful for production of TSG101 peptides.

The invention also provides (a) DNA vectors that contain any of the foregoing tsg101 coding sequences and/or their complements (i.e., antisense); (b) DNA expression vectors that contain any of the foregoing tsg101 coding sequences operatively associated with a regulatory element that directs the expression of the coding sequences; and (c) genetically engineered host cells that contain any of the foregoing TSG101 coding sequences operatively associated with regulatory element that directs the expression of the coding sequences in the host cell for use in producing a TSG101 protein fragment of the invention. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

5.1.1.2. VPS28 Polypeptides

The invention provides human VPS28 protein or fragments or polypeptides of a human VPS28 protein which can be used to modulate the interaction between VPS28 and TSG101 or the interaction between VPS28 and a protein which binds to the C-terminal region of the VPS28 protein during viral assembly and budding process. VPS28 protein, or peptide fragments thereof, can be prepared by standard method known in the art. Preferably, the VPS28 protein is a human VPS28 protein. In a preferred embodiment, the invention provides a fragment of a VPS28 protein which binds TSG101. In one embodiment, the invention provides a fragment of a VPS28 protein comprising the N-terminal region of a VPS28 protein. In a preferred embodiment, the invention provides a fragment of a VPS28 protein comprising amino acids 28 to 59 of a VPS28 protein. In another preferred embodiment, the invention provides a C-terminal deletion mutant of Vps28 protein, in which amino acids 126-167 are deleted. In another preferred embodiment, the invention provides N-terminal deletion mutant of Vps28 protein, in which amino acids 1-27 are deleted. In still another preferred embodiment, the invention provides a fragment of a VPS28 protein comprising amino acids 126-167, or a portion thereof, of a VPS28 protein. In still another preferred embodiment, the invention provides a fragment of a VPS28 protein comprising amino acids 183-221, or a portion thereof, of a VPS28 protein. In another embodiment, the fragment is a fragment of a murine VPS28. The invention also provides any sequence that is at least 30%, 50%, 70%, 90%, or 95% homologous such fragments of a VPS28 protein. In some embodiments of the invention, the VPS28 protein fragments or polypeptides are at least 5, 10, 20, 50, 100 amino acids in length. The VPS28 fragments can be used to interfere with the binding a VPS28 protein with a TSG101 protein.

The invention also provides fragment of a VPS28 protein which is functionally equivalent to any VPS28 fragment described above. Such an equivalent VPS28 fragment may contain deletions, additions or substitutions of amino acid residues within the amino acid sequence encoded by the VPS28 protein gene sequences encoding the VPS28 protein but which result in a silent change, thus producing a functionally equivalent VPS28 protein fragment. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein fragment capable of exhibiting a substantially similar in vivo activity as the endogenous VPS28 protein fragment.

The VPS28 peptide fragments of the invention may be produced by recombinant DNA technology using techniques well known in the art. Thus, methods for preparing the VPS28 polypeptides and peptides of the invention by expressing nucleic acid containing VPS28 gene sequences encoding the VPS28 polypeptide or peptide. Methods which are well known to those skilled in the art can be used to construct expression vectors containing VPS28 polypeptide coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding VPS28 polypeptide sequences may be chemically synthesized using, for example, synthesizers. See, for example, the techniques described in "Oligonucleotide Synthesis", 1984, Gait, M. J. ed., IRL Press, Oxford, which is incorporated herein by reference in its entirety.

The invention also provides portions of a vps28 gene for use for producing any VPS28 protein fragment of the invention described above. In a preferred embodiment, the invention provides a fragment of a vps28 gene comprising the nucleotide region encoding a fragment comprising amino acids 28-59 of a VPS28 protein. In a specific embodiment, the fragment of a VPS28 gene is a fragment of a human vps28 gene, or its murine homolog. The invention also provides any sequence that is at least 30%, 50%, 70%, 90%, or 95% homologous to such fragments of a vps28 gene. In some embodiments of the invention, the fragment of a vps28 gene is at least 20, 25, 40, 60, 80, 100, 500, 1000 bases in length. Such sequences may be useful for production of VPS28 peptides.

The invention also provides (a) DNA vectors that contain any of the foregoing vps28 coding sequences and/or their complements (i.e., antisense); (b) DNA expression vectors that contain any of the foregoing vps28 coding sequences operatively associated with a regulatory element that directs the expression of the coding sequences; and (c) genetically engineered host cells that contain any of the foregoing vps28 coding sequences operatively associated with a regulatory element that directs the expression of the coding sequences in the host cell for use in producing a VPS28 protein fragment of the invention. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

5.1.2. TSG101-VPS28 Protein Complexes

The invention provides TSG101-VPS28 protein complexes, protein complexes of TSG101 fragment and VPS28 fragment, and TSG101-VPS28-GAG protein complexes. Such protein complexes can be prepared by standard method known in the art (see, e.g., PCT Publication WO 02/072790; U.S. Patent Application Publication No. US 2002/0177207, each of which is incorporated herein by reference in its entirety) Such protein complexes can be used in screening assays for screening of agents that can disrupt the interaction between TSG101-VPS28. Such agents can be used for treatment of viral infection, e.g., HIV infection.

5.1.3. Cell Lines that Express TSG101 and/or VPS28 Polypeptides

A variety of host-expression vector systems may be utilized to express the tsg101 and/or vps28 sequences encoding a TSG101 and/or VPS28 protein fragment of the invention. Such host-expression systems represent vehicles by which the coding sequences of interest may be produced and subsequently purified, but also represent cells which may, when transformed or transfected with the appropriate nucleotide coding sequences, exhibit the TSG101 and/or VPS28 of the invention in situ. These include but are not limited to microorganisms such as bacteria (e.g., *E. coli, B. subtilis*) transformed with recombinant bacteriophage DNA, plasmid DNA or cosmid DNA expression vectors containing Tsg101 and/or Vps28 coding sequences; yeast (e.g., *Saccharomyces, Pichia*) transformed with recombinant yeast expression vectors containing the Tsg101 and/or Vps28 coding sequences; insect cell systems infected with recombinant virus expression vectors (e.g., baculovirus) containing the Tsg101 and/or Vps28 coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Tsg101 and/or Vps28 coding sequences; or mammalian cell systems (e.g., COS, CHO, BHK, 293, 3T3, N2a) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the Tsg101 and/or Vps28 protein or a fragment thereof being expressed. For example, when a large quantity of such a protein is to be produced, for the generation of pharmaceutical compositions of Tsg101 and/or Vps28 protein or for raising antibodies to Tsg101 and/or Vps28 protein, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the Tsg101 and/or Vps28 coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 264:5503-5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target protein or polypeptide can be released from the GST moiety.

In an insect system, *Autographa californica* nuclear polyhedrosis virus (AcNPV) is used as a vector to express foreign genes. The virus grows in *Spodoptera frugiperda* cells. The Tsg101 and/or Vps28 gene coding sequence may be cloned individually into non-essential regions (for example the polyhedrin gene) of the virus and placed under control of an AcNPV promoter (for example the polyhedrin promoter). Successful insertion of Tsg101 and/or Vps28 gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the Tsg101 and/or Vps28 gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Tsg101 and/or Vps28 protein or fragment thereof in infected hosts. (E.g., See Logan & Shenk, 1984, Proc. Natl. Acad. Sci. USA 81:3655-3659). Specific initiation signals may also be required for efficient translation of inserted Tsg101 and/or Vps28 coding sequences. These signals include the ATG initiation codon and adjacent sequences. In cases where an entire Tsg101 and/or Vps28 gene, including its own initiation codon and adjacent sequences, is inserted into the appropriate expression vector, no additional translational control signals may be needed. However, in cases where only a portion of the Tsg101 and/or Vps28 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

In addition, a host cell strain may be chosen which modulates the expression of the inserted sequences, or modifies and processes the protein in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the protein may be used. Such mammalian host cells include but are not limited to CHO, VERO, BHK, HeLa, COS, MDCK, 293, 3T3, WI38.

For long-term, high-yield production of recombinant proteins, stable expression is preferred. For example, cell lines which stably express the Tsg101 and/or Vps28 protein or fragment thereof may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Tsg101 and/or Vps28 protein or fragment thereof. Such engineered cell lines may be particularly useful in screening and evaluation of compounds that affect the endogenous activity of the Tsg101 and/or Vps28 protein or fragment thereof.

In another embodiment, the expression characteristics of an endogenous gene (e.g., a Tsg101 and/or Vps28 gene) within a cell, cell line or microorganism may be modified by inserting a DNA regulatory element heterologous to the endogenous gene of interest into the genome of a cell, stable cell line or cloned microorganism such that the inserted regulatory element is operatively linked with the endogenous gene (e.g., a Tsg101 and/or Vps28 gene) and controls, modulates, activates, or inhibits the endogenous gene. For example, endogenous Tsg101 and/or Vps28 genes which are normally "transcriptionally silent", i.e., a Tsg101 and/or Vps28 gene which is normally not expressed, or is expressed only at very low levels in a cell line or microorganism, may be activated by inserting a regulatory element which is capable of promoting the expression of the protein in that cell line or microorganism. Alternatively, transcriptionally silent, endogenous Tsg101 and/or Vps28 genes may be activated by insertion of a promiscuous regulatory element that works across cell types.

A heterologous regulatory element may be inserted into a stable cell line or cloned microorganism, such that it is operatively linked with and activates or inhibits expression of endogenous Tsg101 and/or Vps28 genes, using techniques, such as targeted homologous recombination, which are well known to those of skill in the art, and described e.g., in Chappel, U.S. Pat. No. 5,272,071; PCT Publication No. WO 91/06667 published May 16, 1991; Skoultchi, U.S. Pat. No. 5,981,214; and Treco et al U.S. Pat. No. 5,968,502 and PCT Publication No. WO 94/12650 published Jun. 9, 1994. Alternatively, non-targeted, e.g. non-homologous recombination techniques may be used which are well-known to those of skill in the art and described, e.g., in PCT Publication No. WO 99/15650 published Apr. 1, 1999.

Tsg101 and/or Vps28 gene activation (or inactivation) may also be accomplished using designer transcription factors using techniques well known in the art. Briefly, a designer zinc finger protein transcription factor (ZFP-TF) is made which is specific for a regulatory region of the Tsg101 and/or Vps28 gene to be activated or inactivated. A construct encoding this designer ZFP-TF is then provided to a host cell in which the Tsg101 and/or Vps28 gene is to be controlled. The construct directs the expression of the designer ZFP-TF protein, which in turn specifically modulates the expression of the endogenous Tsg101 and/or Vps28 gene. The following references relate to various aspects of this approach in further detail: Wang & Pabo, 1999, Proc. Natl. Acad. Sci. USA 96, 9568; Berg, 1997, Nature Biotechnol. 15, 323; Greisman & Pabo, 1997, Science 275, 657; Berg & Shi, 1996, Science 271, 1081; Rebar & Pabo, 1994, Science 263, 671; Rhodes & Klug, 1993, Scientific American 269, 56; Pavletich & Pabo, 1991, Science 252, 809; Liu et al., 2001, J. Biol. Chem. 276, 11323; Zhang et al., 2000, J. Biol. Chem. 275, 33850; Beerli et al., 2000, Proc. Natl. Acad. Sci. USA 97, 1495; Kang et al., 2000, J. Biol. Chem. 275, 8742; Beerli et al., 1998, Proc. Natl. Acad. Sci. USA 95, 14628; Kim & Pabo, 1998, Proc. Natl. Acad. Sci. USA 95, 2812; Choo et al., 1997, J. Mol. Biol. 273, 525; Kim & Pabo, 1997, J. Biol. Chem. 272, 29795; Liu et al, 1997, Proc. Natl. Acad. Sci. USA 94, 5525; Kim et al, 1997, Proc. Natl. Acad. Sci. USA 94, 3616; Kikyo et al., 2000, Science 289, 2360; Robertson & Wolffe, 2000, Nature Reviews 1, 11; and Gregory, 2001, Curr. Opin. Genet. Devt. 11, 142.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972-8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

5.2. Antibodies to TSG101 and/or VPS28

The present invention provides antibodies that bind to a TSG101 protein, VPS28 protein, TSG101-VPS28 or TSG101-VPS28-GAG protein complexes. Such antibodies may include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. Such antibodies may be used, for example, in the detection of a TSG101 protein, VPS28 protein, TSG101-VPS28 or TSG101-VPS28-GAG protein complexes in an biological sample and may, therefore, be utilized as part of a diagnostic or prognostic technique whereby patients may be tested for infection by a virus. Such antibodies may also be utilized for the evaluation of the effect of test compounds on modulating TSG101-VPS28 interaction.

Antibodies to TSG101 protein, VPS28 protein, TSG101-VPS28 or TSG101-VPS28-GAG protein complexes may also be used for the inhibition of viral propagation. In preferred embodiments, the antibody of the invention interfere with the interaction between TSG101 and VPS28, and therefore can be used to inhibit viral budding. Thus, such antibodies may, therefore, be utilized as part of treatment methods of viral infection, including HIV infection. In a preferred embodiment, the invention provide an antibody that binds to an epitope in the region of amino acids 28-59 of a VPS28 protein. In another preferred embodiment, the invention provides an antibody that binds to an epitope in the region of amino acids 126-167 of a VPS28 protein. In still another preferred embodiment, the invention provides an antibody that binds to an epitope in the region of amino acids of a VPS28 protein.

5.2.1. Methods of Screening for Antibodies Directed to TSG101 and VPS 28 Proteins and TSG101-VPS28 Protein Complexes The present invention provides methods for screening for antibodies that bind to Tsg101 and/or Vps28 protein. The methods involve screening for antibodies using an appropriate polypeptides of a Tsg101 and/or Vps28 protein. Any fragment of the Tsg101 and/or Vps28 protein, e.g., those described in Section 5.1., can be used to raise the antibody of the invention.

Screening for desired antibody can be accomplished by techniques known in the art. In one embodiment, antibodies which recognize a specific domain of a Tsg101 and/or Vps28, generated hybridomas are assayed for a product which binds to a Tsg101 and/or Vps28 fragment containing such domain.

In another embodiment, an antibody directed against Tsg101 and/or Vps28 protein or a fragment/polypeptide of a Tsg101 and/or Vps28 protein can be identified and isolated by screening a recombinant combinatorial immunoglobulin library (e.g., an antibody phage display library) with the Tsg101 and/or Vps28 protein or a fragment/polypeptide of a Tsg101 and/or Vps28 protein. Kits for generating and screening phage display libraries are commercially available (e.g., Pharmacia Recombinant Phage Antibody System, Catalog No. 27-9400-01; and the Stratagene antigen SurfZAP™ Phage Display Kit, Catalog No. 240612). Additionally, examples of methods and reagents particularly amenable for use in generating and screening antibody display library can be found in, for example, U.S. Pat. Nos. 5,223,409 and 5,514,548; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734. A phage display library permits selection of desired antibody or antibodies from a very large repertoire of specificities. An additional advantage of a phage display library is that the nucleic acids encoding the selected antibodies can be obtained conveniently, thereby facilitating subsequent construction of expression vectors.

For selection of an antibody that specifically binds a particular isoform of Tsg101 and/or Vps28 but which does not specifically bind other isoforms of Tsg101 and/or Vps28, by any of the above mentioned methods of this section, one can select on the basis of positive binding to the desired isoform of Tsg101 and/or Vps28 and a lack of binding to the other isoforms. In a preferred embodiment, the sequence of a Tsg101 and/or Vps28 fragment used for the selection of antibodies is a sequence not comprised by other isoforms of Tsg101 and/or Vps28 whose activities are to be preserved.

5.2.2. Methods of Production of Antibodies

Described herein are methods for the production of antibodies capable of specifically recognizing one or more Tsg101 and/or Vps28 protein epitopes or epitopes of conserved variants or peptide fragments of the Tsg101 and/or Vps28 proteins, e.g, peptide fragments described in Section 5.1.

For the production of antibodies against a Tsg101 and/or Vps28 protein, various host animals may be immunized by injection with a Tsg101 and/or Vps28 protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as a Tsg101 and/or Vps28 protein, or an antigenic functional derivative thereof. For the production of polyclonal antibodies, host animals such as those described above, may be immunized by injection with Tsg101 and/or Vps28 protein or a fragment thereof supplemented with adjuvants as also described above.

Monoclonal antibodies, which are homogeneous populations of antibodies to a particular antigen, such as a Tsg101 and/or Vps28 protein, or an antigenic functional derivative thereof, may be obtained by any technique which provides for the production of antibody molecules by continuous cell lines in culture. These include, but are not limited to, the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334:544-546) can be adapted to produce single chain antibodies against Tsg101 and/or Vps28 proteins. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275-1281) to allow rapid and easy identification of monoclonal Fab fragments with the desired specificity.

5.3. Uses of TSG101, VPS28, and Interaction of TSG101 and VPS28

The invention provides methods and compositions for treatment of viral infections, including HIV infection. The invention provides methods and compositions for inhibiting or reducing viral release thereby treating viral infection in an animal, e.g., a human, by modulating, e.g., interfering with, TSG101-VPS28 interaction. The invention also provides methods and compositions for inhibiting or reducing viral release thereby treating viral infection in an animal, e.g., a human, by modulating the expression of tsg101 or vps28 gene. The invention also provides methods and compositions for inhibiting or reducing viral release thereby treating viral infection in an animal, e.g., a human, by modulating, e.g., interfering with, the interaction of VPS28 to a protein which binds to the C-terminal region of the VPS28 protein during viral assembly and budding process.

The invention provides methods and compositions for utilizing the Tsg101 and Vps28 protein complexes for identifying proteins or other molecules that modulate, e.g., inhibit, the interaction between Tsg101 and Vps28. The invention also provides methods and compositions for utilizing the Tsg101 and/or Vps28 protein and antibodies for screening for agents that modulate Tsg101 and/or Vps28 expression. The invention further provides methods and compositions for utilizing the Tsg101 and/or Vps28 protein and antibodies for screening for agents that are useful in modulating, e.g., inhibiting, interaction of Vps28 and a protein which binds to the C-terminal region of the VPS28 protein during viral assembly and budding process.

5.3.1. Treatment of Viral Infection by Modulating TSG101-VPS28 Interaction

Diseases or disorders that can be treated or prevented by the use of the methods and compositions of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I (HIV-I), and human immunodeficiency virus type II (HIV-II), any picornaviridae, enteroviruses, caliciviridae, any of the Norwalk group of viruses, togaviruses, such as Dengue virus, alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein-Barr virus, human herpesvirus-6, cercopithecine herpes virus 1 (B virus), and poxviruses.

Additional diseases or disorders that can be treated or prevented by the use of the method and composition of the present invention include, but are not limited to, those caused by influenza virus, human respiratory syncytial virus, Dengue virus, measles virus, herpes simplex virus type 2, poliovirus I VP1, HIV I, hepatitis B virus, pseudorabies virus, pseudorabies virus II, swine rotavirus, swine parvovirus, bovine viral diarrhea virus, Newcastle disease virus, swine flu hemagglutinin, swine flu virus, foot and mouth disease virus, hog colera virus, swine influenza virus, African swine fever virus, infectious bovine rhinotracheitis virus, infectious laryngotracheitis virus, a glycoprotein of La Crosse virus, neonatal calf diarrhea virus, Venezuelan equine encephalomyelitis virus, punta toro virus, murine leukemia virus, mouse mammary tumor virus, equine influenza virus or equine herpesvirus, bovine respiratory syncytial virus or bovine parainfluenza virus.

5.3.1.1. Methods of Modulating TSG101-VPS28 Interaction

The invention provides methods of treating a viral infection, e.g., HIV infection, in an animal by modulating the interaction between TSG101 and VPS28. In preferred embodiments of the invention, a therapeutically sufficient amount of an agent which inhibits or reduces TSG101 and VPS28 binding is administered to an animal, e.g., a human, who has been infected by a virus, e.g., a HIV virus. Any molecules of the invention, e.g., molecules described in Sections 5.1 and 5.2., supra, and Section 5.3.2, infra, which inhibits or reduces binding between TSG101 and VPS28 can be used for this purpose. Pharmaceutical formulation, dosage, and route of administration that can be used in the invention are described in Section 5.4., infra.

In a preferred embodiment, the administered agent comprises a VPS28 polypeptide which binds TSG101. In one embodiment, the VPS28 polypeptide is a full length VPS28 protein. In another embodiment, the VPS28 polypeptide comprises a fragment of a VPS28 protein comprising the N-terminal region of a VPS28 protein. In a preferred embodiment, the VPS28 polypeptide comprises amino acids 28 to 59 of a VPS28 protein. In another preferred embodiment, the VPS28 polypeptide is a C-terminal deletion mutant of Vps28 protein, in which amino acids 126-167 are deleted. In still another preferred embodiment, the VPS28 polypeptide is an N-terminal deletion mutant of Vps28 protein, in which amino acids 1-27 are deleted.

In another preferred embodiment, the administered agent comprises a TSG101 polypeptide which binds VPS28. In one embodiment, the TSG101 polypeptide is a fragment of a TSG101 protein not comprising the UEV domain. In a preferred embodiment, the TSG101 polypeptide comprises the coiled-coil domain of a TSG101 protein. In another preferred embodiment, the TSG101 polypeptide comprises the C-terminal domain of a TSG101 protein.

In still another preferred embodiment, the administered agent comprises an antibody which interferes with the binding of TSG101 and VPS28. In one embodiment, the antibody is a TSG101 antibody. In another embodiment, the antibody is a VPS28 antibody. In a preferred embodiment, the VPS28 antibody binds to an epitope within amino acids 28-59 of the VPS28 protein.

In still another preferred embodiment, the agent comprises an antibody which interferes with the binding of VPS28 to a protein which binds to the C-terminal region of the VPS28 protein during viral assembly and budding process. In a preferred embodiment, the antibody binds to an epitope within amino acids 126-167 of the VPS28 protein.

5.3.1.2. Methods of Modulating Expression of TSG101 and/or VPS28 Gene

The invention also provides methods of treating a viral infection, e.g., HIV infection, by modulating the expression of tsg101 gene and/or vps28 gene. A variety of therapeutic approaches may be used in accordance with the invention to modulate expression of the Tsg101 and/or Vps28 gene in vivo. For example, antisense DNA molecules may be engineered and used to block translation of Tsg101 and/or Vps28 mRNA in vivo. Alternatively, ribozyme molecules may be designed to cleave and destroy the Tsg101 and/or Vps28 mRNAs in vivo. In another alternative, oligonucleotides designed to hybridize to the 5' region of the Tsg101 and/or Vps28 gene (including the region upstream of the coding sequence) and form triple helix structures may be used to block or reduce transcription of the Tsg101 and/or Vps28 gene. In still another alternative, siRNA or shRNA targeting TSG101 or VPS28 may be used to block or reduce transcription of the Tsg101 and/or Vps28 gene. Oligonucleotides can also be designed to hybridize and form triple helix structures with the binding site of a negative regulator so as to block the binding of the negative regulator and to enhance the transcription of the Tsg101 and/or Vps28 gene. In yet another alternative, nucleic acid encoding the full length wild-type Tsg101 and/or Vps28 message may be introduced in vivo into cells which otherwise would be unable to produce the wild-type Tsg101 and/or Vps28 fragment in sufficient quantities or at all. In yet another embodiment, a heterologous regulatory element may be inserted before the coding sequence of a Tsg101 and/or Vps28 gene, such that it is operatively linked with and activates expression of the endogenous Tsg101 and/or Vps28 gene.

In a preferred embodiment, the antisense, ribozyme, and triple helix nucleotides are designed to inhibit the translation or transcription of one or more of Tsg101 and/or Vps28 isoforms with minimal effects on the expression of other genes that may share one or more sequence motif with a Tsg101 and/or Vps28. To accomplish this, the oligonucleotides used should be designed on the basis of relevant sequences unique to Tsg101 and/or Vps28.

For example, and not by way of limitation, the oligonucleotides should not fall within those region where the nucleotide sequence of Tsg101 and/or Vps28 is most homologous to that of other genes. Instead, it is preferred that the oligonucleotides fall within the portion of the sequence of Tsg101 and/or Vps28 that does not encode a PHD domain. In the case of antisense molecules, it is preferred that the sequence be chosen from the list above. It is also preferred that the sequence be at least 18 nucleotides in length in order to achieve sufficiently strong annealing to the target mRNA sequence to prevent translation of the sequence. Izant et al., 1984, Cell, 36:1007-1015; Rosenberg et al., 1985, Nature, 313:703-706.

In the case of the "hammerhead" type of ribozymes, it is also preferred that the target sequences of the ribozymes be chosen from the list above. Ribozymes are RNA molecules which possess highly specific endoribonuclease activity. Hammerhead ribozymes comprise a hybridizing region which is complementary in nucleotide sequence to at least part of the target RNA, and a catalytic region which is adapted to cleave the target RNA. The hybridizing region contains nine (9) or more nucleotides. Therefore, the hammerhead ribozymes of the present invention have a hybridizing region which is complementary to the sequences listed above and is at least nine nucleotides in length. The construction and production of such ribozymes is well known in the art and is described more fully in Haseloff et al., 1988, Nature, 334: 585-591.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO 88/04300 by University Patents Inc.; Been et al., 1986, Cell, 47:207-216). The Cech endoribonucleases have an eight base pair active site which hybridizes to a target RNA sequence whereafter cleavage of the target RNA takes place.

In the case of oligonucleotides that hybridize to and form triple helix structures at the 5' terminus of the Tsg101 and/or Vps28 gene and can be used to block transcription, it is preferred that they be complementary to those sequences in the 5' terminus of Tsg101 and/or Vps28 which are not present in other Tsg101 and/or Vps28 related genes. It is also preferred that the sequences not include those regions of the Tsg101 and/or Vps28 promoter which are even slightly homologous to that of other Tsg101 and/or Vps28 related genes. The foregoing compounds can be administered by a variety of methods which are known in the art including, but not limited to the use of liposomes as a delivery vehicle. Naked DNA or RNA molecules may also be used where they are in a form which is resistant to degradation such as by modification of the ends, by the formation of circular molecules, or by the use of alternate bonds including phosphothionate and thiophosphoryl modified bonds. In addition, the delivery of nucleic acid may be by facilitated transport where the nucleic acid molecules are conjugated to poly-lysine or transferrin. Nucleic acid may also be transported into cells by any of the various viral carriers, including but not limited to, retrovirus, vaccinia, AAV, and adenovirus.

Alternatively, a recombinant nucleic acid molecule which encodes, or is, such antisense, ribozyme, triple helix, or Tsg101 and/or Vps28 molecule can be constructed. This nucleic acid molecule may be either RNA or DNA. If the nucleic acid encodes an RNA, it is preferred that the sequence be operatively attached to a regulatory element so that sufficient copies of the desired RNA product are produced. The regulatory element may permit either constitutive or regulated transcription of the sequence. In vivo, that is, within the cells or cells of an organism, a transfer vector such as a bacterial plasmid or viral RNA or DNA, encoding one or more of the RNAs, may be transfected into cells e.g. (Llewellyn et al., 1987, J. Mol. Biol., 195:115-123; Hanahan et al. 1983, J. Mol. Biol., 166:557-580). Once inside the cell, the transfer vector may replicate, and be transcribed by cellular polymerases to produce the RNA or it may be integrated into the genome of the host cell. Alternatively, a transfer vector containing sequences encoding one or more of the RNAs may be transfected into cells or introduced into cells by way of micromanipulation techniques such as microinjection, such that the transfer vector or a part thereof becomes integrated into the genome of the host cell.

Post-transcriptional gene silencing (PTGS) or RNA interference (RNAi) can also be used to block expression of Tsg101 and/or Vps28 (Guo et al., 1995, Cell 81:611-620; Fire et al., 1998, Nature 391:806-811; Grant, 1999, Cell 96:303-306; Tabara et al., 1999, Cell 99:123-132; Zamore et al., 2000, Cell 101:25-33; Bass, 2000, Cell 101:235-238; Petcherski et al., 2000, Nature 405:364-368; Elbashir et al., Nature 411:494-498; Paddison et al., Proc. Natl. Acad. Sci. USA 99:1443-1448). After delivery into the cells, the dsRNAs are cut by nuclease into 21-23 nucleotide fragments which hybridize to the homologous region of their corresponding mRNAs to form double-stranded segments which are degraded by nuclease. Preferably, dsRNAs have a hybridizing region which is complementary to the sequences listed above and is at least 23 nucleotides in length. The dsRNAs are transfected into a cell or tissue sample. Any standard method for introducing nucleic acids into cells can be used for this purpose. In a preferred embodiment, short hairpin RNA gene silencing (Paddison et al., 2002, Genes Dev 16, 948-58) is used to silence VPS28 gene. In this embodiment, the pU6-hVps28-shRNA was constructed by PCR of U6 promoter using U6 promoter reverse primer: GGTGTTTCGTCCTTTCCACAA (SEQ ID NO:1) and AAAAAAGATACAGCGATTGAGATTGCCCTTGTCATCAAGCTTCACGACAAGGG CAACCTCAACCGCTGCATCGGTGTTTCGTCCTTTCCACAA (SEQ ID NO:2) primers and cloned into pCR 2.1 (Invitrogen) vector. In another embodiment, the siRNA targeting the human Vps28 gene hays the following sequence: sense, GCCCUGGAGAAGGCCUACATT (SEQ ID NO:3); anti-sense, UGUAGGCCUUCUCCAGGGCTT (SEQ ID NO:4). As shown in FIG. 1, co-transfection pNL4-3 with a DNA vector containing the U6 promoter and siRNA sequences targeting nucleotides 359-386 of the Vps28 coding sequence inhibited HIV-1 release by 66% (lane 6) compared to co-transfection with a control vector containing only the U6 promoter (lane 5). In repeated experiments, 60-80% inhibition in HIV-1 release using shRNA targeting Vps28. The shRNA targeting the Vps28 coding region reduced the expression of Vps28 by approximately 80% (lane 8) compared to the control vector (lane 7).

The expression of Tsg101 and/or Vps28 genes can also be activated or enhanced. In one embodiment, a heterologous regulatory element may be inserted before the coding sequence of a Tsg101 and/or Vps28 gene, such that it is operatively linked with and activates expression of the endogenous Tsg101 and/or Vps28 gene, using techniques, such as targeted homologous recombination, which are well known to those of skill in the art, and described e.g., in Chappel, U.S. Pat. No. 5,272,071; PCT publication No. WO 91/06667, published May 16, 1991; Skoultchi U.S. Pat. No. 5,981,214; Treco et al U.S. Pat. No. 5,968,502 and PCT publication No. WO 94/12650, published Jun. 9, 1994. Alternatively, non-targeted e.g., non-homologous recombination techniques which are well-known to those of skill in the art and described, e.g., in PCT publication No. WO 99/15650, published Apr. 1, 1999, may be used.

In another embodiment, the expression of a Tsg101 and/or Vps28 gene is enhanced by blocking the binding of a negative regulator (i.e., a repressor). Any agent that binds to such site and inhibit the binding of a regulator molecule, including but not limited to peptides or nucleic acid molecules, can be used for this purpose.

5.3.1.3. Gene Therapy Based on TSG101 and VPS28 Interaction

The invention also provides methods for treating a viral infection, e.g., HIV infection, in an animal by gene therapy. A variety, of gene therapy approaches may be used in accordance with the invention to modulate expression of the Tsg101 and/or Vps28 gene in vivo. In an alternative, nucleic acid encoding a fragment of the Tsg101 and/or Vps28 protein may be introduced in vivo into cells so as to modulate, e.g., interfere with, the Tsg101 and Vps28 interaction.

In a specific embodiment, nucleic acids comprising a sequence encoding a fragment of Tsg101 and/or Vps28 or functional derivative thereof, are administered by way of gene therapy. Gene therapy refers to therapy performed by the administration of a nucleic acid to a subject. In this embodiment of the invention, the nucleic acid produces its encoded protein that mediates a therapeutic effect by modulating the interaction between Tsg101 and Vps28 and/or by modulating the expression of Tsg101 and/or Vps28.

Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, New York; and Kriegler, 1990, Gene Transfer and Expression, A Laboratory Manual, Stockton Press, New York.

In a preferred aspect, the therapeutic comprises a Tsg101 and/or Vps28 nucleic acid that is part of an expression vector that expresses a Tsg101 and/or Vps28 or fragment or chimeric protein thereof in a suitable host. In particular, such a nucleic acid has a promoter operably linked to the Tsg101 and/or Vps28 coding region, said promoter being inducible or constitutive, and, optionally, tissue-specific. In another particular embodiment, a nucleic acid molecule is used in which the Tsg101 and/or Vps28 coding sequences and any other desired sequences are flanked by regions that promote homologous recombination at a desired site in the genome, thus providing for intrachromosomal expression of the Tsg101 and/or Vps28 nucleic acid (see e.g., Koller and Smithies, 1989, Proc. Natl. Acad. Sci. U.S.A. 86:8932-8935; Zijlstra et al., 1989, Nature 342:435-438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol.

Chem. 262:4429-4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination, (Koller and Smithies, 1989, Proc. Natl. Acad. Sci. U.S.A. 86:8932-8935; Zijlstra et al., 1989, Nature 342:435-438).

In a specific embodiment, a viral vector that contains the Tsg101 and/or Vps28 nucleic acid is used. For example, a retroviral vector can be used (see Miller et al., 1993, Meth. Enzymol. 217:581-599). These retroviral vectors have been modified to delete retroviral sequences that are not necessary for packaging of the viral genome and integration into host cell DNA. The Tsg101 and/or Vps28 nucleic acid to be used in gene therapy is cloned into the vector, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. Genet. and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993, Current Opinion in Genetics and Development 3:499-503) present a review of adenovirus-based gene therapy. Bout et al. (1994, Human Gene Therapy 5:3-10) demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234.

Adeno-associated virus (AAV) has also been proposed for use in gene therapy (Walsh et al., 1993, Proc. Soc. Exp. Biol. Med. 204:289-300).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled person in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a Tsg101 and/or Vps28 nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (PCT Publication WO 94/08598), and neural stem cells (Stemple and Anderson, 1992, Cell 71:973-985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see e.g., Kodo et al., 1984, J. Clin. Invest. 73:1377-1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. U.S.A. 79:3608-3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods that can be adapted for use to deliver a nucleic acid encoding a Tsg101 and/or Vps28 fragment of the invention or functional derivative thereof are described below.

5.3.2. Methods of Screening for Agents

The invention provides methods for screening for agents that regulate Tsg101 and/or Vps28 expression or modulate interaction of Tsg101 and Vps28.

5.3.2.1. Screening Assays

The following assays are designed to identify compounds that bind to Tsg101 and/or Vps28 proteins, bind to other cellular proteins that interact with a Tsg101 and/or Vps28 protein, bind to cellular constituents, e.g., proteins, that are affected by a Tsg101 and/or Vps28 protein, or bind to compounds that interfere with the interaction of the Tsg101 and Vps28 and to compounds which modulate the activity of Tsg101 and/or Vps28 gene (i.e., modulate the level of Tsg101 and/or Vps28 gene expression and/or modulate the level of Tsg101 and/or Vps28 protein activity). Assays may additionally be utilized which identify compounds which bind to Tsg101 and/or Vps28 gene regulatory sequences (e.g., promoter sequences), see e.g., Platt, K. A., 1994, J. Biol. Chem. 269:28558-28562, which is incorporated herein by reference in its entirety, which may modulate the level of Tsg101 and/or Vps28 gene expression. Compounds may include, but are not limited to, small organic molecules which are able to affect expression of the Tsg101 and/or Vps28 gene.

Compounds may include, but are not limited to, peptides such as, for example, soluble peptides, including but not limited to, Ig-tailed fusion peptides, and members of random peptide libraries; (see, e.g., Lam, K. S. et al., 1991, Nature 354:82-84; Houghten, R. et al., 1991, Nature 354:84-86), and combinatorial chemistry-derived molecular library made of D- and/or L-configuration amino acids, phosphopeptides (including, but not limited to members of random or partially degenerate, directed phosphopeptide libraries; see, e.g., Songyang, Z. et al., 1993, Cell 72:767-778), antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof), and small organic or inorganic molecules.

Compounds identified via assays such as those described herein may be useful, for example, in regulating the interaction of Tsg101 and Vps28. Assays for testing the effectiveness of compounds are discussed, below.

In vitro systems may be designed to identify compounds capable of binding the Tsg101 and/or Vps28 fragments of the invention. Compounds identified may be useful, for example, in modulating the activity of wild type and/or mutant Tsg101 and/or Vps28, may be utilized in screens for identifying compounds that disrupt normal Tsg101 and Vps28 interactions, or may in themselves disrupt such interactions.

The principle of the assays used to identify compounds that bind to the Tsg101 and/or Vps28 fragments involves preparing a reaction mixture of the Tsg101 and/or Vps28 fragments and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring Tsg101 and/or Vps28 protein or a fragment thereof or the test substance onto a solid phase and detecting Tsg101 and/or Vps28 fragment/test compound complexes anchored on the solid phase at the end of the reaction. In one embodiment of such a method, the Tsg101 and/or Vps28 fragment may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for Tsg101 and/or Vps28 fragment or the test compound to anchor any complexes formed in solution, and a labeled antibody specific for the other component of the possible complex to detect anchored complexes.

The Tsg101 and Vps28 interact to form a complex which is important in viral release. Compounds that disrupt Tsg101 and Vps28 binding may be useful in inhibiting TSG101 and VPS28 binding, and thereby inhibiting or reducing viral release. Such compounds may include, but are not limited to molecules such as peptides, and the like, as described above.

The basic principle of the assay systems used to identify compounds that interfere with the interaction between the Tsg101 and Vps28 involves preparing a reaction mixture containing a Tsg101 and/or Vps28 fragment, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of Tsg101 or Vps28 fragment and its binding partner. Control reaction mixtures are incubated without the test compound or with a placebo. The formation of any complexes between the Tsg101 and Vps28 fragment is then detected. The formation of a complex in the control reaction, but not in the reaction mixture containing the test compound, indicates that the compound interferes with the interaction of the Tsg101 and Vps28 proteins. Additionally, complex formation within reaction mixtures containing the test compound and normal Tsg101 and Vps28 proteins may also be compared to complex formation within reaction mixtures containing the test compound and a mutant Tsg101 and/or Vps28 protein. This comparison may be important in those cases wherein it is desirable to identify compounds that disrupt interactions of mutant but not normal Tsg101 and/or Vps28 proteins.

The assay for compounds that interfere with the interaction of the Tsg101 and Vps28 fragments can be conducted in a heterogeneous or homogeneous format. Heterogeneous assays involve anchoring either the Tsg101 or Vps28 fragment onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the Tsg101 and Vps28 fragments, e.g., by competition, can be identified by conducting the reaction in the presence of the test substance; i.e., by adding the test substance to the reaction mixture prior to or simultaneously with the Tsg101 and Vps28 proteins. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the Tsg101 or Vps28 fragment is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the Tsg101 or Vps28 fragment and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the Tsg101 and Vps28 is prepared in which either the Tsg101 or Vps28 fragment is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt Tsg101 and Vps28 interaction can be identified.

In a particular embodiment, the Tsg101 or Vps28 fragment can be prepared for immobilization using recombinant DNA techniques described in above. For example, the Tsg101 or Vps28 coding region can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above. This antibody can be labeled with the radioactive isotope $^{125}I$, for example, by methods routinely practiced in the art. In a heterogeneous assay, e.g., the GST-Tsg101 or Vps28 fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the Tsg101 and Vps28 can be detected by measuring the amount of radioactivity that remains associated with the glutathione-agarose beads. A successful inhibition of the interaction by the test compound will result in a decrease in measured radioactivity.

Alternatively, the GST-Tsg101 and Vps28 fusion protein can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the Tsg101/Vps28 can be detected by adding the labeled antibody and measuring the radioactivity associated with the beads.

In another embodiment of the invention, these same techniques can be employed using peptide fragments that correspond to the binding domains of the Tsg101 and/or Vps28 protein, in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the binding partner is obtained, short gene segments can be engineered to express peptide fragments of the protein, which can then be tested for binding activity and purified or synthesized.

For example, and not by way of limitation, a Tsg101 or Vps28 fragment can be anchored to a solid material as described above by making a GST-Tsg101 or Vps28 fusion protein and allowing it to bind to glutathione agarose beads. The interactive binding partner can be labeled with a radioactive isotope, such as $^{35}S$, and cleaved with a proteolytic enzyme such as trypsin. Cleavage products can then be added to the anchored GST-Tsg101 or Vps28 fusion protein and allowed to bind. After washing away unbound peptides, labeled bound material, representing the binding partner binding domain, can be eluted, purified, and analyzed for amino acid sequence by well-known methods. Peptides so identified can be produced synthetically or fused to appropriate facilitative proteins using recombinant DNA technology.

VPS28 also interacts with other proteins during viral release. Compounds that disrupt Vps28 binding with such other protein may also be useful in inhibiting or reducing viral release. Such compounds can be identified using any of the assays described above, e.g., by replacing TSG101 with such other protein.

5.3.2.2. Screening Compounds that have Antiviral Effects

Any agents that regulate the expression of Tsg101 and/or Vps28 gene and/or the interaction of Tsg101 and/or Vps28 protein with its binding partners, e.g., compounds, antibodies to Tsg101 and/or Vps28 protein, and so on, can be further screened for its ability to inhibit or reduce viral release from infected cells. Any suitable assays known in the art can be used for this purpose. In one embodiment, the assay is a standard HIV-1 replication assay. In one embodiment, cells are infected by HIV-1 MN virus in D-10 medium containing 20 ug/ml DEAE dextran for 2 hr in 37° C. CO2 incubator. After a suitable period, e.g., two hours, of incubation, cells are washed twice by D-10 medium, and then cultured in D-10 medium. The agent to be screened is then applied to the infected cells. HIV-1 replication is monitored by measuring the amount of p24 in the culture medium using HIV-1 p24 ELISA kit (PerkinElmer Life Sciences, Inc.).

5.3.2.3. Compounds Identified

The compounds identified in the screen include compounds that demonstrate the ability to selectively modulate the interaction of Tsg101 and Vps28 and inhibit viral budding. These compounds include but are not limited to Tsg101 and/or Vps28 peptide fragment and homologues, analogues, and deletions thereof. The compounds identified in the screen also include compounds that demonstrate the ability to modulate the expression of Tsg101 and/or Vps28 gene and inhibit viral budding. These compounds include but are not limited to antisense, ribozyme, triple helix, dsRNAs/siRNAs, antibody, and polypeptide molecules and small organic or inorganic molecules.

The compounds identified in the screen also include compounds that modulate interaction of Tsg101 and/or Vps28 with other proteins or molecules, e.g., a HIV-1 GAG protein or a protein which binds to the C-terminal region of the VPS28 protein during viral assembly and budding process. In one embodiment, the compounds identified in the screen are compounds that modulate the interaction of a Tsg101 and/or Vps28 protein with its interaction partner. In another embodiment, the compounds identified in the screen are compounds that modulate the interaction of Tsg101 and/or Vps28 gene with a transcription regulator.

5.3.3. Detection of TSG101 and/or VPS28 Fragments

Antibodies directed against wild type or mutant Tsg101 and/or Vps28 fragments or conserved variants or peptide fragments thereof, e.g., those discussed in Section 5.1., may also be used as diagnostics and prognostics of viral infection, e.g., by detecting the presence of such fragment on cell surface. Such diagnostic methods, may also be used to detect abnormalities in the level of Tsg101 and/or Vps28 gene expression, or abnormalities in the structure and/or temporal, tissue, cellular, or subcellular location of Tsg101 and/or Vps28 fragment.

The antibodies and immunoassay methods described below have also important in vitro applications in assessing the efficacy of treatments for viral infection in which Tsg101 and Vps28 proteins are involved. Antibodies, or fragments of antibodies, such as those described below, may be used to screen potentially therapeutic compounds in vitro to determine their effects on Tsg101 and/or Vps28 gene expression, Tsg101 and/or Vps28 peptide production, and Tsg101 and Vps28 interaction. The compounds which have beneficial effects on treating viral infection in which Tsg101 and Vps28 proteins are involved, e.g., capable of reducing the number of budding particles, can be identified, and a therapeutically effective dose determined.

In vitro immunoassays may also be used, for example, to assess the efficacy of cell-based gene therapy for regulating the expression level of Tsg101 and/or Vps28. Antibodies directed against Tsg101 and/or Vps28 peptides may be used in vitro to determine the level of Tsg101 and/or Vps28 gene expression achieved in cells genetically engineered to produce Tsg101 and/or Vps28 peptides. Given that evidence disclosed herein indicates that the Tsg101 and Vps28 fragment are intracellular fragments, such an assessment is, preferably, done using cell lysates or extracts. Such analysis will allow for a determination of the number of transformed cells necessary to achieve therapeutic efficacy in vivo, as well as optimization of the gene replacement protocol.

The tissue or cell type to be analyzed may include those which are known, or suspected, to be infected by a virus. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cell taken from culture may be a necessary step in the assessment of cells to be used as part of a cell-based gene therapy technique or, alternatively, to test the effect of compounds on the expression of the Tsg101 and/or Vps28 gene.

Preferred diagnostic methods for the detection of Tsg101 and/or Vps28 fragments or conserved variants or peptide fragments thereof, may involve, for example, immunoassays wherein the Tsg101 and/or Vps28 fragments or conserved variants or peptide fragments are detected by their interaction with an anti-Tsg101 and/or Vps28 fragment-specific antibody.

For example, antibodies, or fragments of antibodies, such as those described above useful in the present invention may be used to quantitatively or qualitatively detect infected cells by the presence of Tsg101 and/or Vps28 fragments or conserved variants or peptide fragments thereof on their surfaces. This can be accomplished, for example, by immunofluorescence techniques employing a fluorescently labeled antibody (see below, this Section) coupled with light microscopic, flow cytometric, or fluorimetric detection. Such techniques are especially useful in viral infection where Tsg101 and/or Vps28 fragments are recruited to the cell surface during the viral budding process.

The antibodies (or fragments thereof) useful in the present invention may, additionally, be employed histologically, as in immunofluorescence or immunoelectron microscopy, for in situ detection of Tsg101 and/or Vps28 fragments or conserved variants or peptide fragments thereof. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the Tsg101 and/or Vps28 fragment, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for Tsg101 and/or Vps28 fragments or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying Tsg101 and/or Vps28 fragments or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled Tsg101 and/or Vps28 protein specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tub, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-Tsg101 and/or Vps28 fragment antibody may be determined according to well known methods. Those skilled in the art will be able to determine operative and optimal assay conditions for each determination by employing routine experimentation.

One of the ways in which the Tsg101 and/or Vps28 gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller, A. et al., 1978, J. Clin. Pathol. 31:507-520; Butler, J. E., 1981, Meth. Enzymol. 73:482-523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect Tsg101 and/or Vps28 gene peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.4. Pharmaceutical Formulations and Routes of Administration

The compounds that are determined to modulate Tsg101 and/or Vps28 gene expression or modulating Vps28 interaction with Tsg101 or another protein can be administered to a patient at therapeutically effective doses to treat or ameliorate viral infection. A therapeutically effective dose refers to that amount of the compound sufficient to result in amelioration of the viral infection.

5.4.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.4.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.4.3. Routes of Administration

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

5.4.4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

6. EXAMPLE

In the following example an embodiment of the invention in which methods and compositions for inhibiting HIV-1 budding are described. The example is presented by way of illustration of the present invention, and is not intended to limit the present invention in any way.

Vps28 is important for HIV-1 release. To address the question of whether Vps28 is important for HIV-1 release, a DNA-based strategy (shRNA) was used for the delivery of siRNA (Paddison et al., 2002, *Genes Dev* 16, 948-58) against Vps28 and its effect on HIV-1 release in transfected 293T cells was examined. For this purpose a DNA vector (pU6-Vps28) containing the U6 promoter and siRNA-generating sequences targeting nucleotides 359 to 386 of the Vps28 coding region was constructed. As shown in FIG. 1, co-transfection of pNL4-3 with pU6-Vps28 or the control vector pGEM-U6 did not affect HIV-1 expression in transfected 293T cells (FIG. 1A, lanes 2 and 3). Co-transfection of pNL4-3 with pU6-Vps28 inhibited HIV-1 release by 66% (lane 6) when compared to co-transfection with pGEM-U6 (lane 5). Targeting of the shRNA to the Vps28 coding region reduced the expression of Vps28 by approximately 80% (FIG. 1B, lane 2) when compared to the control vector (FIG. 1B, lane 1). In repeated experiments, a 50-72% inhibition of HIV-1 release using the shRNA targeting Vps28 (FIG. 1C) was observed.

A Vps28 mutant blocks HIV-1 release. As an initial step in screening for Vps28 mutants that may inhibit HIV-1 release, an N-terminal 59-amino acid deletion mutant (Vps28ΔN) and a C-terminal 43-amino acid deletion mutant (Vps28ΔC) of Vps28 were constructed. Both constructs express Vps28 proteins fused with a Flag epitope tag at the C-terminus for easy detection. The effect of the N-terminal and C-terminal deletion mutants of Vps28 on HIV-1 release was studied in transfected 293T cells. Expression of the C-terminal deletion mutant (Vps28ΔC) reduced the release of HIV-1 by 67% (FIG. 2A, lane 10) when compared to the control vector (FIG. 2A, lane 7). On the other hand, expression of the N-terminal deletion mutant (Vps28ΔN) had little effect on the release of HIV-1 (FIG. 2A, lane 9). Expression of exogenous full-length Vps28 had a moderate effect (58% reduction) on the release of HIV-1 (FIG. 2A, lane 8). In repeated experiments, Vps28ΔC inhibited HIV-1 release by 53-75% (FIG. 2B).

The interaction of these mutants with TSG101 was also evaluated. Both mutants, as well as the full-length Vps28, were immunoprecipitated from transfected 293T cells by the anti-Flag antibody. TSG101 was co-precipitated with the full-length Vps28 (FIG. 2C, lane 6). Deletion of C-terminal 43 amino acids of Vps28 had no significant effect on its interaction with TSG101 (FIG. 2C, lane 8). However, deletion of the N-terminal 52 amino acids from Vps28 significantly reduced its interaction with TSG101 (FIG. 2C, lane 7), despite the mutant protein was efficiently precipitated (FIG. 2C, lane 11). Expression of exogenous full length or mutant Vps28 had no significant effect on the expression of TSG101 in transfected 293T cells (FIG. 2C, lanes 1 to 4).

To further identify the region of Vps28 that is important for its interaction with Tsg101 and for the inhibition of virus release, several more Vps28 mutant constructs were evaluated. Deletion of the N-terminal 27 amino acids did not significantly affect its interaction with Tsg101, and expression of this protein reduced HIV-1 release by about 72% (FIG. 3). Internal deletion of amino acids 19 to 59 abolished Vps28 interaction with Tsg101, and this mutant did not affect HIV-1 release (FIG. 3). Deletion of another C-terminal region (amino acids 126 to 167) of Vps28 also did not affect its interaction with Tsg101 and this mutant inhibited HIV-1 release by about 63% (FIG. 3). Altogether, these results suggested that the N-terminal region of Vps28, and especially amino acids 28 to 59, plays an important role in the interaction with Tsg101, whereas the C-terminal half of Vps28 apparently does not. Mutant Vps28s that interacted with Tsg101 inhibited HIV-1 release, whereas mutant Vps28s that failed to interact with Tsg101 did not inhibit HIV-1 release.

Effect of Vps28 mutation on ESCRT-I-like complex formation. To study the effect of Vps28 mutation on the formation of an ESCRT-I-like complex, cell extracts from pVps28ΔC- and pVps28-transfected cells and from control vector-transfected 293T cells were prepared and analyzed by size exclusion chromatography. Tsg101 migrated as a single species with an estimated molecular mass of 350 kDa in the control vector-transfected cells (FIG. 4). However, Tsg101 displayed an additional smaller peak (about 200 kDa) in cells transfected with Vps28ΔC (FIG. 4). Similar results were also observed in pVps28-transfected cells (FIG. 4). It has been reported that over-expression of a myc-tagged Vps28 also disrupts ESCRT-I-like complexes (Bishop et al., 2002, J Cell Biol 157, 91-101). These results suggest that expression of Vps28ΔC or exogenous Vps28 disrupted some of the ESCRT-I-like complexes, and this disruption may have contributed to the observed inhibition of HIV-1 release.

Vps28 interacts with HIV-1 Gag. In yeast, Vps28 and TSG101 form a functional ESCRT-1-like complex that is critical for the sorting of vesicular proteins (Katzmann et al., 2001, Cell 106, 145-55; Bishop et al., 2001, *J Biol Chem* 276, 11735-42). The data reported above suggest that Vps28 and its interaction with TSG101 are important for HIV-1 release. It is possible that Vps28 is recruited to the site of virus assembly through its interaction with TSG101. To test this possibility, co-immunoprecipitation experiments were performed. A Vps28 expression vector (pVps28) was co-transfected with pNL4-3 or the PTAP-mutant (Huang et al., 1995, *J Virol* 69, 6810-8). Two days after transfection, cell lysates were immunoprecipitated with a goat anti-$p7^{Gag}$ antiserum, and the precipitated materials were analyzed by Western blot using anti-Flag antibody to detect the Flag-tagged Vps28. Both the wild-type Gag and PTAP-mutant Gag molecules were precipitated by the anti $p7^{Gag}$ antiserum (FIG. 5A, lanes 2 and 3). Flag epitope-tagged Vps28 was detected in the pNL4-3 cell lysates immunoprecipitated by the anti $p7^{Gag}$ antiserum (FIG. 5A, lane 2) but not in the PTAP-mutant cell lysates (FIG. 5A, lane 3). Comparable Flag-tagged Vps28 molecules were detected in both pNL4-3 cell lysates and PTAP-mutant cell lysates (FIG. 5A, lanes 5 and 6).

Vps28 is incorporated into HIV-1. It was observed that Vps28 was co-precipitated with HIV-1 Gag (FIG. 5A), possibly through interaction with TSG101. To determine whether the interaction between HIV-1 Gag and the ESCRT-I-like complex occurs only transiently during virus budding, and the complex is subsequently removed from released virions, or that some components of the ESCRT-I-like complex are incorporated into HIV-1 virions, full-length Vps28 and the N-terminal (Vps28ΔN) or C-terminal (Vps28ΔC) deletion mutants of Vps28 with pNL4-3 were co-expressed in the cells. Virions were collected and adjusted to contain comparable levels of p24. Both the full-length form and the C-terminal deletion mutant of Vps28 were detected in the released HIV-1 virions (FIG. 5B, lanes 7 and 8). However, the N-terminal deletion mutant of Vps28 was not detected in the released virions (lane 6), despite the fact that the intracellular expression level of the N-terminal deletion mutant of Vps28 (lane 10) was higher than those of full-length Vps28 (lane 12) or the C-terminal deletion mutant of Vps28 (lane 11).

A Vps28 mutant inhibits HIV-1 replication in T cells. To test whether the functional interaction between HIV-1 Gag and TSG101/Vps28 could be a vulnerable target during HIV-1 replication, Jurkat (CD4+) cells were transduced with a retroviral expression vector expressing Vps28ΔC or with a control vector. They were then infected with HIV-1MN. Viral replication was monitored by measuring the secretion of p24 into the supernatants of infected cells from day 1 to day 5. HIV-1 replication in control vector-transduced Jurkat cells was first detected at day 1 after infection and found to increase thereafter (FIG. 5). No HIV-1 replication was detected in Vps28ΔC-transduced Jurkat cells on day 1 (FIG. 5). From day 2 to day 5, HIV-1 replication in Vps28ΔC-transduced Jurkat cells was reduced by 67% to 88% when compared to that in control Jurkat cells (FIG. 5). Since Vps28ΔC-transduced Jurkat cells were not separated from untransduced cells, this incomplete suppression of HIV-1 replication was probably produced by only a portion of the cells expressing Vps28ΔC.

Discussion

The results of this example demonstrated that Vps28 plays an important role in HIV-1 release: First, HIV-1 release was inhibited by reducing the expression of intracellular Vps28 by interference with shRNA targeting the coding region of Vps28. Second, several Vps28 mutants inhibited HIV-1 release. Specifically, an N-terminal region of Vps28 (amino acids 28 to 59) was shown to be critical for this inhibition. This region was also important for Vps28 interaction with Tsg101. Third, Vps28 could be co-immunoprecipitated with Gag from transfected cells. This co-precipitation was not detected in an HIV-1 Gag mutant lacking the PTAP motif. Interaction between HIV-1 Gag and Vps28 during virus assembly was further supported by the observation that Vps28 was incorporated into released virions.

Studies using yeast and mammalian systems have indicated that TSG101 and Vps28 interact with each other to form an ESCRT-I complex which functions in vacuolar protein sorting. In this example it was shown that expression of mutant forms of Vps28ΔC disrupted the ESCRT-I complex and inhibited HIV-1 release. These data indicate that an interaction between Vps28 and TSG101, perhaps in the form of an ESCRT-I-like complex, plays an important role in HIV-1 release. It has been estimated that the ESCRT-I-like complex in HIV-1 contains a single Tsg101 molecule and multiple copies of Vps28; therefore, the Vps28 mutants could act as trans-dominant negative mutants. These mutant Vps28s could still interact with Tsg101 but lost the ability to interact with other components of the ESCRT-I-like complex, producing an aberrant and smaller Tsg101-containing complex. Consistent with this idea, Vps28 mutants that had lost the ability to interact with Tsg101 were unable to inhibit HIV-1 release. Altering the ratio between Tsg101 and Vps28, as in the case of over-expression of exogenous Vps28 (see, e.g., FIG. 4), also disrupted ESCRT-I formation. Over-expression of Tsg101 could also inhibit HIV-1 release. A proper ratio between Tsg101 and Vps28 may be important for the formation and function of ESCRT-I complex. In addition to HIV-1, other enveloped viruses such as Ebola virus (Martin-Serrano et. al., 2001, Nature Medicine 7:1313-19) also require Tsg101 for efficient virus release.

It is worth noting that only the Vps28 mutants that maintained their ability to interact with Tsg101 were able to inhibit HIV-1 release. A critical region in Vps28 that is required for interaction with Tsg101 maps to amino acids 28 to 59. Amino acids in this region have the potential to form an alpha-helical domain, as identified by several secondary structure prediction programs. Interestingly, the C-terminal region of Tsg101 that is important for interaction with Vps28 also has the potential to form an alpha-helical domain (Bishop et al., 2001, *J Biol Chem* 276, 11735-42).

Expression of mutant Vps28 molecules not only reduced HIV-1 release in 293T cells but also inhibited HIV-1 replication in CD4+ T cells (FIG. 6). Virus release is potentially an attractive target for anti-viral intervention. The HIV-1 late domain motif, PTAP, is highly conserved and is essential for viral replication in T cell lines (Gottlinger et al., 1991, *Proc Natl Acad Sci USA* 88, 3195-9; Demirov et al., 2002, J Virol 76, 105-17; Dettenhofer et al., 1999, *J Virol* 73, 4696-704) and PBMC (Dettenhofer et al., 1999, *J Virol* 73, 4696-704). ESCRT-I complexes normally function in the endosomal compartment, whereas HIV-1 budding occurs at the plasma membrane. Thus, selective targeting of ESCRT-I function at the site of virus budding could be explored without significantly affecting normal processes in the host cells.

Materials and Methods

Plasmid Vector Construction. The human Vps28-Flag fusion construct was cloned from a PCR-amplified product into the p3XFLAG-CMV-14 vector (Sigma, E4901). The forward primer 5'-TAGAAGCTTATGTTTCATGGGATCCCAGC-3' (SEQ ID NO:5) and reverse primer 5'-GCTTCTAGAGGCATGCAGGAAGCGGTTGAA-3' (SEQ ID NO:6) contained HindIII site and XbaI site, respectively, at their ends. The Flag-tagged Vps28 mutants pVps28ΔN1, pVps28ΔN, pVps28D1, pVps28D2, and pVps28ΔC were generated by PCR. The following forward and reverse primers were used to amplify and clone Vps28 mutants into p3XFLAG-CMV-14: Vps28ΔN1, forward 5'-TAGAAGCT-TATGAACGCCCGGGAGAGGGA-3' (SEQ ID NO:7) and reverse 5'-GCTTCTAGAGGCATGCAGGAAGCGGT-TGAA-3' (SEQ ID NO:8); Vps28ΔN, forward 5'-TAGAAGCTTATGTGTGTCTCCCCCAGCGAG-3' (SEQ ID NO:9) and reverse 5'-GCTTCTAGAGGCATG-CAGGAAGCGGTTGAA-3' (SEQ ID NO:10); Vps28D1, forward 5'-CCTGGGAACAAGCCGTGTGTCTC-CCCCAGCG-3' (SEQ ID NO:11) and reverse 5'-CGCTGGGGGAGACACACGGCTTGTTCCCAGG (SEQ ID NO:12); Vps28D2, forward 5'-GACGA-CAAGGGCAACCTCAGCCACCTCCCACCC-3' (SEQ ID NO:13) and reverse 5'-GGGTGGGAGGTGGCTGAGGT-TGCCCTTGTCGTC-3' (SEQ ID NO:14); and Vps28ΔC, forward 5'-TAGAAGCTTATGTTTCATGGGATCCCAGC-3' (SEQ ID NO:15) and reverse 5'-GCTTCTAGACTGGCT-GACCGTCTGGCG-3' (SEQ ID NO:16). Phoenix retrovirus vector-expressing Vps28-Flag (pBMN-I-Neo-hVps28ΔC) was constructed by inserting the Vps28ΔC-Flag gene into the pBMN-Z-I-Neo vector (from Dr. Garry Nolan, Stanford University). The hVps28ΔC-Flag gene was amplified by PCR using pVps28ΔC as template. The forward primer 5'-ATG-GAAGATCTCGTGTACGGTGGGAGGTC-3' (SEQ ID NO:17) and reverse primer 5'-ATCCGCTCGAGGGTCA-CAGGGATGCCAC-3' (SEQ ID NO:18) contained BglII site and XhoI sites, respectively. The PCR product was digested with BglII and XhoI and inserted into the pBMN-Z-I-Neo vector, which had been digested with BamHI and SalI. A DNA vector that could generate siRNA targeting Vps28 was constructed using the method of short hairpin RNA (shRNA) gene silencing (Paddison et al., 2002, *Genes Dev* 16, 948-58). PCR products containing U6 promoter and Vps28 sequences were amplified using the forward primer GGTGTTTCGTC-CTTTCCACAA (SEQ ID NO:1) and reverse primer AAAAAAGATACAGCGATTGAGATTGC-CCTTGTCATCAAGCTTCACGACAAGGG CAACCT-CAACCGCTGCATCGGTGTTTCGTCCTTTCCACAA (SEQ ID NO:2), then cloned into the pCR 2.1 (Invitrogen) vector.

Cell Culture, Transfection, and Virus Purification. 293T and Phoenix retrovirus helper cell lines ( ) were maintained in Dulbecco's modified Eagle's medium (DMEM, Invitrogen) with 10% fetal bovine serum and antibiotics and passaged upon confluence. Jurkat cells were maintained in RPMI 1640 medium (Invitrogen) supplemented with 10% fetal bovine serum with penicillin/streptomycin. DNA transfection was carried out using Lipofectamine 2000 (Invitrogen) or Transit-LT1 (Minis) as described by the manufacturers. Virion-associated viral proteins were prepared from cell culture supernatants by removal of cellular debris by centrifugation at 3,000 rpm for 30 min in a Sorvall RT 6000B centrifuge and filtration through a 0.2-mm pore-size membrane. Virus particles were concentrated by centrifugation through a 30% sucrose cushion at 100,000×g for 2 h in a Sorvall Ultra80 ultracentrifuge.

Immunoblotting. At 48 h after transfection, the transfected cells were collected, and cell lysates and viral lysates were prepared as previously described (9, 19). Cells ($1\times10^5$) were lysed in 1× loading buffer (0.08 M Tris, pH 6.8, with 2.0% SDS, 10% glycerol, 0.1 M dithiothreitol, and 0.2% bromophenol blue). Samples were boiled for 10 min and proteins were separated by SDS-PAGE. Proteins were transferred onto two separate nitrocellulose membranes by passive diffusion for 16 h, producing identical mirror image blots. Membranes were probed with either mouse anti-HIV-1 P24 monoclonal antibody (Mab) (NIH AIDS reagent bank), mouse anti-Flag M2 Mab (Sigma), goat anti-HIV-1 p7 (Yu et al., 1995), or rabbit polyclonal antiserum against TSG101 (Li et al., 2001). Secondary antibodies were alkaline phosphatase-conjugated anti-human, anti-rabbit, anti-mouse, or anti-goat IgG (Jackson Immunoresearch, Inc., West Grove, Pa.), and staining was carried out with 5-bromo-4-chloro-3-indolyl phosphate (BCIP) and nitro blue tetrazolium (NBT) solutions prepared from chemicals obtained from Sigma.

Co-immunoprecipitation. Cells were harvested and washed twice with cold PBS, then lysed with PBS containing 0.5% Triton X-100 and protease inhibitor cocktail (Roche) at 4° C. for 1 h. Cell lysates were clarified by centrifugation at 12000×g for 30 min at 4° C. For Vps28 co-precipitation, anti-Flag-agarose (Sigma) was mixed with the pre-cleared cell lysates and shaken at 4° C. for 3 h. The reaction mixture was then washed three times with cold PBS. For Gag co-precipitation, the anti-p7 (Liza) antibody was first mixed with the pre-cleared cell lysates at 4° C. for 3 h. Protein G-agarose (Roche) was then added to the reaction mixture and shaken at 4° C. for 3 h. Reaction mixtures were washed three times with PBS and eluted with 0.1M glycine-HCl buffer, pH 3.5. The eluted materials were subsequently analyzed by Western blotting.

HIV-1 Replication assay. An M-MuLV-derived retroviral expression vector pBMN-Z-1-Neo (from Dr. Garry Nolan, Stanford University), which expresses both LacZ and Neo under the control of the retroviral LTR, was used to construct a retroviral expression vector for Vps28ΔC by replacing LacZ. Both the Vps28ΔC expression vector pBMN-Vps28ΔC and pBMN-Z-I-Neo control vector were transfected into Phoenix helper cells (from Dr. Garry Nolan) to generate infectious retroviruses. At 48 h after transfection, retroviral supernatant from each transfected helper cell culture was used to transduce Jurkat cells. Jurkat cells were washed twice with PBS 24 h later and infected with 30 ng of p24-equivalent HIV-1 MN overnight. Cells were then washed twice with R-10 medium and maintained in fresh R-10 medium. HIV-1 replication was monitored by measuring the amount of p24 in the culture supernatant using an HIV-1 p24 ELISA kit (PerkinElmer Life Sciences, Inc.).

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for reducing viral budding and infectivity from a mammalian cell infected by human immunodeficiency virus (HIV) comprising a Gag-PTAP [SEQ ID NO.: 19] motif, said method comprising contacting said mammalian cell with an antibody that binds a mammalian VPS28 protein at an epitope in a region of amino acids 28-59 and thereby inhibits TSG101-VPS28-HIV Gag binding interaction, wherein said antibody is present in an amount sufficient to inhibit release of HIV virions from said cell.

2. The method of claim 1, wherein said mammalian cell is a human cell.

3. The method of claim 1, wherein said antibody is a monoclonal antibody.

* * * * *

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<223> OTHER INFORMATION: U6 promoter reverse primer

<400> SEQUENCE: 1

ggtgtttcgt cctttccaca a                                                21


<210> SEQ ID NO 2
<211> LENGTH: 93
<212> TYPE: DNA
<213> ORGANISM: Artificial Sequence
<220> FEATURE:
<223> OTHER INFORMATION: U6 promoter reverse primer

<400> SEQUENCE: 2

aaaaaagata cagcgattga gattgccctt gtcatcaagc ttcacgacaa gggcaacctc      60

aaccgctgca tcggtgtttc gtcctttcca caa                                   93


<210> SEQ ID NO 3
<211> LENGTH: 21
<212> TYPE: DNA
<213> ORGANISM: Artificial Sequence
<220> FEATURE:
<223> OTHER INFORMATION: siRNA (combined DNA/RNA)

<400> SEQUENCE: 3

gcccuggaga aggccuacat t                                                21


<210> SEQ ID NO 4
<211> LENGTH: 21
<212> TYPE: DNA
<213> ORGANISM: Artificial Sequence
<220> FEATURE:
<223> OTHER INFORMATION: siRNA (combined DNA/RNA)

<400> SEQUENCE: 4

uguaggccuu cuccagggct t                                                21


<210> SEQ ID NO 5
<211> LENGTH: 29
<212> TYPE: DNA
<213> ORGANISM: Artificial Sequence
<220> FEATURE:
<223> OTHER INFORMATION: human Vps28-Flag fusion construct forward
      primer

<400> SEQUENCE: 5

tagaagctta tgtttcatgg gatcccagc                                        29


<210> SEQ ID NO 6
<211> LENGTH: 30
<212> TYPE: DNA
<213> ORGANISM: Artificial Sequence
<220> FEATURE:
<223> OTHER INFORMATION: human Vps28-Flag fusion construct reverse
      primer

<400> SEQUENCE: 6

gcttctagag gcatgcagga agcggttgaa                                       30
```

<210> SEQ ID NO 7
<211> LENGTH: 29
<212> TYPE: DNA
<213> ORGANISM: Artificial Sequence
<220> FEATURE:
<223> OTHER INFORMATION: Vps28 delta N1 forward primer

<400> SEQUENCE: 7
tagaagctta tgaacgcccg ggagaggga 29

<210> SEQ ID NO 8
<211> LENGTH: 30
<212> TYPE: DNA
<213> ORGANISM: Artificial Sequence
<220> FEATURE:
<223> OTHER INFORMATION: Vps28 delta N1 reverse primer

<400> SEQUENCE: 8
gcttctagag gcatgcagga agcggttgaa 30

<210> SEQ ID NO 9
<211> LENGTH: 30
<212> TYPE: DNA
<213> ORGANISM: Artificial Sequence
<220> FEATURE:
<223> OTHER INFORMATION: Vps28 delta N forward primer

<400> SEQUENCE: 9
tagaagctta tgtgtgtctc ccccagcgag 30

<210> SEQ ID NO 10
<211> LENGTH: 30
<212> TYPE: DNA
<213> ORGANISM: Artificial Sequence
<220> FEATURE:
<223> OTHER INFORMATION: Vps28 delta N reverse primer

<400> SEQUENCE: 10
gcttctagag gcatgcagga agcggttgaa 30

<210> SEQ ID NO 11
<211> LENGTH: 31
<212> TYPE: DNA
<213> ORGANISM: Artificial Sequence
<220> FEATURE:
<223> OTHER INFORMATION: Vps28D1 forward primer

<400> SEQUENCE: 11
cctgggaaca agccgtgtgt ctcccccagc g 31

<210> SEQ ID NO 12
<211> LENGTH: 31
<212> TYPE: DNA
<213> ORGANISM: Artificial Sequence
<220> FEATURE:
<223> OTHER INFORMATION: Vps28D1 reverse primer

<400> SEQUENCE: 12
cgctggggga gacacacggc ttgttcccag g 31

<210> SEQ ID NO 13
<211> LENGTH: 33
<212> TYPE: DNA
<213> ORGANISM: Artificial Sequence
<220> FEATURE:
<223> OTHER INFORMATION: Vps28D2 forward primer -continued

<400> SEQUENCE: 13
gacgacaagg gcaacctcag ccacctccca ccc 33

<210> SEQ ID NO 14
<211> LENGTH: 33
<212> TYPE: DNA
<213> ORGANISM: Artificial Sequence
<220> FEATURE:
<223> OTHER INFORMATION: Vps28D2 reverse primer

<400> SEQUENCE: 14
gggtgggagg tggctgaggt tgcccttgtc gtc 33

<210> SEQ ID NO 15
<211> LENGTH: 29
<212> TYPE: DNA
<213> ORGANISM: Artificial Sequence
<220> FEATURE:
<223> OTHER INFORMATION: Vps28 delta C forward primer

<400> SEQUENCE: 15
tagaagctta tgtttcatgg gatcccagc 29

<210> SEQ ID NO 16
<211> LENGTH: 27
<212> TYPE: DNA
<213> ORGANISM: Artificial Sequence
<220> FEATURE:
<223> OTHER INFORMATION: Vps28 delta C reverse primer

<400> SEQUENCE: 16
gcttctagac tggctgaccg tctggcg 27

<210> SEQ ID NO 17
<211> LENGTH: 29
<212> TYPE: DNA
<213> ORGANISM: Artificial Sequence
<220> FEATURE:
<223> OTHER INFORMATION: pVps28 delta C forward primer

<400> SEQUENCE: 17
atggaagatc tcgtgtacgg tgggaggtc 29

<210> SEQ ID NO 18
<211> LENGTH: 28
<212> TYPE: DNA
<213> ORGANISM: Artificial Sequence
<220> FEATURE:
<223> OTHER INFORMATION: pVps28 delta C reverse primer

<400> SEQUENCE: 18
atccgctcga gggtcacagg gatgccac 28

<210> SEQ ID NO 19
<211> LENGTH: 4
<212> TYPE: PRT
<213> ORGANISM: HIV-1

<400> SEQUENCE: 19

Pro Thr Ala Pro
1

<210> SEQ ID NO 20
<211> LENGTH: 4
<212> TYPE: PRT
<213> ORGANISM: RSV

<400> SEQUENCE: 20

Pro Pro Pro Tyr
1

<210> SEQ ID NO 21
<211> LENGTH: 4
<212> TYPE: PRT
<213> ORGANISM: EIAV
<220> FEATURE:
<221> NAME/KEY: VARIANT
<222> LOCATION: 2, 3
<223> OTHER INFORMATION: Xaa = Any Amino Acid

<400> SEQUENCE: 21

Tyr Xaa Xaa Leu
1